US007722721B2

(12) United States Patent
Heikkilä et al.

(10) Patent No.: US 7,722,721 B2

(45) Date of Patent: *May 25, 2010

(54) SEPARATION METHOD

(75) Inventors: Heikki Heikkilä, Espoo (FI); Katja Häkkä, Espoo (FI); Juho Jumppanen, West Sussex (GB); Pia Saari, Espoo (FI); Nina Nurmi, Helsinki (FI); Vili Ravanko, Clinton, IA (US)

(73) Assignee: Danisco Sweeteners Oy (FI)

( * ) Notice: Subject to any disclaimer, the term of this patent is extended or adjusted under 35 U.S.C. 154(b) by 396 days.

This patent is subject to a terminal disclaimer.

(21) Appl. No.: 11/713,861

(22) Filed: Mar. 5, 2007

(65) Prior Publication Data

US 2007/0155677 A1 Jul. 5, 2007

Related U.S. Application Data

(62) Division of application No. 10/875,460, filed on Jun. 24, 2004, now abandoned.

(60) Provisional application No. 60/486,221, filed on Jul. 10, 2003.

(30) Foreign Application Priority Data

Jun. 27, 2003 (FI) .................................. 20030963

(51) Int. Cl.
*C13J 1/06* (2006.01)
*C07H 1/06* (2006.01)

(52) U.S. Cl. ...................................... 127/46.2; 536/128

(58) Field of Classification Search ....................... None
See application file for complete search history.

(56) References Cited

U.S. PATENT DOCUMENTS

| | | | |
|---|---|---|---|
| 925,380 A | 5/1963 | Donnelly | |
| 4,156,076 A * | 5/1979 | Dahlgren | 536/124 |
| 4,471,114 A | 9/1984 | Sherman et al. | |
| 4,772,334 A | 9/1988 | Hatanaka et al. | |
| 6,451,123 B1 | 9/2002 | Saska et al. | |
| 7,037,378 B2 * | 5/2006 | Jumppanen et al. | 127/30 |

FOREIGN PATENT DOCUMENTS

| | | |
|---|---|---|
| EP | 1046719 A1 | 10/2000 |
| WO | WO 99/53088 | 10/1999 |
| WO | WO 00/42225 A1 | 7/2000 |
| WO | WO 03/056038 | 7/2003 |

OTHER PUBLICATIONS

H. Caruel L. Rigal, et al. (1991) "Carbohydrate Separation by Liquid-Exchange Liquid Chromatography", *Journal of Chromatography*, 558, pp. 89-104.

M. Sinner, et al. (1975) "Automated Quantitative Analysis of Wood Carbohydrates by Borate Complex Ion Exchange Chromatography", *Wood Science and Technology*, pp. 307-322.

Japanese Patent Publication No. 06-201671, published on Jul. 22, 1994 (Abstract only).

Chemical Abstract No. (CAN) 121:250635 AN 1994:650635 Caplus.
Chemical Abstract No. (CAN) 88:59903 AN 1978:59903 Caplus.
Chemical Abstract No. (CAN) 107:178514 AN 1987:578514 Caplus.
Chemical Abstract No. (CAN) 119:141489 AN 1993:541489 Caplus.
Chemical Abstract No. (CAN) 76:35416 AN 1972:35416 Caplus.
Chemical Abstract No. (CAN) 84:32847 AN 1976:32847 Caplus.
Chemical Abstract No. (CAN) 83:81769 AN 1975:481769 Caplus.
Chemical Abstract No. (CAN) 81:90026 AN 1974:490026 Caplus.

* cited by examiner

*Primary Examiner*—Elli Peselev
(74) *Attorney, Agent, or Firm*—Scully, Scott, Murphy & Presser, P.C.

(57) ABSTRACT

The invention relates to a process of recovering galactose from a solution derived from plant-based biomass. In the process of the invention, the starting solution is subjected to one or more chromatographic fractionation steps, which may carried out with a strongly basic anion exchange resin and optionally with a strongly acid cation exchange resin, in any desired sequence, followed by recovering at least one fraction enriched in galactose. The galactose fraction thus obtained is further purified by crystallization to obtain crystalline galactose. The invention also relates to non-animal derived crystalline D-galactose.

29 Claims, 9 Drawing Sheets

SEPARATION METHOD

CROSS REFERENCE TO RELATED APPLICATIONS

The present application is a divisional of application Ser. No. 10/875,460 filed on Jun. 24, 2004, now abandoned, which claims benefit of U.S. Provisional application Ser. No. 60/486,221 filed Jul. 10, 2003.

FIELD OF THE INVENTION

The invention relates to a process of recovering galactose from a solution containing the same, especially from plant-based biomass-derived solutions containing galactose as an admixture with other sugars and carbohydrates. The invention also relates to non-animal derived crystalline galactose, especially plant-based crystalline D-galactose.

BACKGROUND OF THE INVENTION

Galactose is a monosaccharide, which is mostly found in the milk sugar or lactose, where galactose is bound to glucose. In some sour milk products, lactose has been decomposed into glucose and galactose.

Galactose has many applications in the pharmaceutical field and in food technology. In the pharmaceutical field, galactose is useful for example as a pharmaceutical intermediate for several medicines. Furthermore, galactose is also useful as a stabilizer in intravenous solutions for medical use. In food technology, galactose has been found useful for example as a potential energy source in sports drinks. Galactose is also useful in cell culture media as a nutrient or as an inducer in the fermentation.

Galactose is as a rule obtained by hydrolyzing lactose (a disaccharide consisting of glucose and galactose), which is found in dairy products, such as milk. Recently, for example due to the BSE disease, there is an increased interest to produce galactose of non-dairy and non-animal origin.

British Patent 925 380, Joseph Donelly (published May 8, 1963) discloses a process based on crystallization for purifying crude anhydrous (D)(+)-galactose, which has been produced by the degradation of an oligosaccharide, such as lactose, melibiose and raffinose. The purification process comprises dissolving the crude galactose in methyl alcohol or ethyl alcohol or a mixture thereof with water, removing the undissolved impurities and recovering galactose from the solution by crystallization, optionally followed by recrystallization. The purity of the galactose product has not been reported.

WO 99/53088, Deva Processing Services Ltd (published 21 Oct. 1999) discloses a process for the production of galactose from galactose-containing disaccharide or polysaccharide, such as lactose, by hydrolysis and enzymatic treatment. The galactose obtained by this process is not crystallized. It is recited in the reference that it is extremely difficult to separate contaminants from galactose so that galactose with a pharmaceutical grade purity would be obtained.

Galactose is rather rare in plant-based materials, but it has been found in not very abundant amounts in various plants as a multicomponent mixture with other sugars and carbohydrates. Galactose has been found for instance in wood resources, where galactose is, present as an admixture with other carbohydrates and lignin components. Softwood hemicelluloses are especially rich in galactose. Galactose has also been found in various natural gums and pectin-based materials.

Wood resources, for example, may thus be potential sources for the recovery of plant-based galactose. Spent liquors obtained from acid wood-pulping processes, especially liquors from softwood pulping processes can be mentioned as examples of potential starting materials for the recovery of galactose.

It is known in the state of the art to recover galactose from various plant-based raw materials using methods selected for example from extraction, hydrolysis and treatment with adsorbents and cation and anion exchangers, followed by crystallization. Chromatographic methods for the recovery of galactose-containing solutions from plant-based materials are also known in the state of the art. However, these chromatographic methods for the recovery of galactose-containing solutions generally provide galactose as a mixture with other closely-related sugars. Galactose has not been recovered from said sugar mixtures.

EP 1 046 719 A1, Cargill B. V. (published 25 Oct. 2000) recites that rare sugars, for example arabinose, rhamnose, fucose and mannose are unwanted in galactose preparations, because the presence of these components will limit for example the scope of food applications in which the galactose preparations may be used. The EP publication discloses a process based on hydrolysis for manufacturing D-galactose from an oligosaccharide-containing legume composition which contains D-galactose mainly in chemical combination with D-glucose and/or D-fructose. The oligo-saccharide-containing material is typically derived from soybeans, rapeseeds or sunflower seeds or mixtures thereof. In the examples, a galactose preparation containing D-galactose in an amount of 3 to 10% on a dry weight basis was recovered. In accordance with Example 4 of the reference, the D-galactose content of the preparation may be increased by chromatography. The galactose preparation obtained by the process is not crystallized.

U.S. Pat. No. 6,451,123 B1, Saska, M., Board of Supervisors of Louisiana State University of Agricultural and Mechanical College (published 17 Sep. 2002) discloses a method of separating a carbohydrate selected from xylose, mannose, galactose, arabinose, glucose, xylitol, arabitol, galactitol and mannitol from an aqueous phase comprising said carbohydrate and at least one other non-identical component (a sugar or a sugar alcohol). The aqueous phase from which the carbohydrates are separated may be a soft-wood liquor, a hardwood liquor or a hydrolysate thereof, for example. It is recited that the separation is carried out using a strong base anion exchange resin in an anion form, which is other than hydroxyl form. The resin used for the separation is conditioned with a sufficient concentration of hydroxyl ion. In a typical application of the method, a resin in a chloride form is used. In this process, galactose is not recovered.

U.S. Pat. No. 6,451,123 B1 mentioned above refers to man-nose/galactose separation with a strong acid cation selected from $Ca^{2+}$ and $Pb^{2+}$ (page 2, Table II, lines 65 and 66) disclosed by Caruel H. et al.

Caruel, H. et. al. have studied carbohydrate separation in "Carbohydrate separation by ligand-exhange liquid chromatography: correlation between the formation of sugar-cation complexes and the elution order", J. Chromatography 558(1), pp. 89-104 (1991). It is recited that carbohydrate separation (hexoses, pentoses and corresponding polyols) was studied by liquid chromatography using ligand exchange on a strong acid cation-exchange resin column with water as the eluent. Seven cations ($Ca^{2+}$, $Sr^{2+}$, $Ba^{2+}$, $Pb^{2+}$, $Y^{3+}$, $La^{3+}$ and $Pr^{3+}$) were tested.

U.S. Pat. No. 3,471,329, Laevosan-Gesellschaft Chem. Pharm Industrie Frank & Dr. Freudl (published Oct. 7, 1969)

discloses a process for the separation of different sugars from a mixture thereof, comprising reacting a cation exchange resin with hydrazine, and then contacting an aqueous-alcoholic solution of said mixture of sugars with the hydrazine-containing cation exchange resin, followed by washing the sugar-containing resin to fractionate the sugars and obtain the individual sugars present in said sugar mixture in the different fractions. The cation exchange resin may contain highly acid active groups, such as sulphate, carboxyl or phosphite groups. The separation of fructose and galactose is disclosed in Example 3 of said reference. It is also recited in Example 3 that the galactose fractions gave pure crystallized galactose after crystallization. However, the feed solution is not a hemicellulose hydrolysate.

U.S. Pat. No. 5,084,104, Cultor Ltd, Heikkilä et al. (published Jan. 28, 1992) discloses a process for the production of a high purity xylose fraction from a xylose-rich solution further containing other monosaccharides, using chromatographic fractionation with a strong base anion exchange resin in sulphate form. Galactose is not recovered in this process.

U.S. Pat. No. 4,772,334, Kureha Kagaku Kogyo Kabushiki Kaisha (published Sep. 20, 1988) discloses a process for producing highly pure rhamnose from gum arabic by hydrolyzing gum arabic with a mineral acid to form a liquid hydrolysate comprising L-rhamnose, L-arabinose and D-galactose and subjecting the neutralized and clarified hydrolysate to strongly cationic ion-exchange chromatography to separate D-galactose and L-arabinose from L-rhamnose using a mixture of water and organic solvent as an eluant. In the examples, a $Na^+$ form resin is used. Galactose is not recovered.

U.S. Pat. No. 4,857,642, UOP (published 15 Aug. 1989) discloses a process for separating arabinose from an aqueous feed mixture containing arabinose and at least one other monosaccharide from the group consisting of aldoses and ketoses by contacting the feed mixture with an X-zeolite adsorbent containing ammonium cations. Said other monosaccharide is typically selected from glucose, xylose, galactose and mannose. It is recited that arabinose is selectively absorbed by the X-zeolite adsorbent. Galactose is not re-covered.

Bollini, M & Galli, R ("Separation and determination of the sugars of bisulfite liquors", Stn. Sper. Cellul., Carta Fibre Tess. Veg. Artif., Milan, Italy. Ind. Carta (1975), 13(10), 392-4) have identified and determined mannose, glucose, galactose, arabinose, xylose, hexoses and pentoses in a bisulfite liquor after the separation of lignosulphonates. The liquor was treated with EtOH, the precipitate centrifuged, lignosulphonates separated, purified with cation and anion exchange resins and subjected to gas chromatographic and colori-metric determinations.

Sinner, M., Simatupang, M. H. & Dietrichs, H. H. ("Automated Quantitative Analysis of Wood Carbohydrates by Borate Complex Ion Exchange Chromatography", Wood Science and Technology, 1975, pp. 307 to 322) describe a simple automated analytical method for the separation and quantitative determination of sugars from acidic and enzymatic hydrolysates of wood polysaccharides via borate complex ion exchange chromatography. The sugars separated in this way may include mannose, fructose, arabinose, galactose, xylose, glucose and disaccharides like xylobiose, cellobiose and sucrose.

Guihard, L., Dendene, K. & Bariou, B. ("Sugar separation by low pressure chromatography", Lab. GPSA, ENSCR, Rennes Beaulieu, Fr. Recents Progrés en Genie des Procédés (1991), 5 (15, Procédés Sep.), 167-72 disclose the separation of lactose from other milk sugars using AG 50W-X8 cation exchanger. A syrup containing galactose, lactose and lactulose was first eluted on the resin in $Na^+$ form, eliminating the galactose fraction. The product containing lactose and lactulose was then eluted on the resin in $Ca^{2+}$ form giving lactulose in practically pure form. Galactose is not recovered in this process.

Indian Patent IN 158940 A, Council of Scientific and Industrial Research (India), (published 21 Feb. 1987) discloses a process for the preparation of pure D-galactose from green Aegle marmelos fruit-gum. In this process, said fruit material is subjected to two-step hydrolysis with $H_2SO_4$, followed by deionization treatment with Amberlite IR 120 ($H^+$) and IR-4B ($OH^-$). The product thus obtained is purified with activated carbon, and the solution is heated to a temperature of less than 40° C. under reduced pressure to give a syrup. The syrup is treated with 100 ml hot MeOH and 8-10 ml water, to crystallize D-galactose.

Ingle, T. R, Kulkarni, V. R, Vaidya. S. H. & Pai, M. U., Natl. Chem. Lab, Poona, India, Res. Ind. (1976), 21(4), 243-6 disclose a commercial process for the preparation of D-galactose from cashew nut shells. In this process, the cashew nutshell material is subjected to aqueous extraction, hydrolysis with $H_2SO_4$, concentration to a syrup, extraction, decolorization with activated charcoal, concentration and crystallization, followed by drying and powdering of the crystalline D-galactose.

Serdyuk, L. V, Dudkin, M. S., Gerzhov, A. F., Odess. Tekhnol. Inst. Pishch. Prom. im. Lomonosova, Odessa, USSR, Izv. Vyssh. Ucheb. Zaved. Pishch. Tekhnol. (1974), (2), 28-30 disclose potato as raw material for the production of concentrated solutions of simple sugars, including galactose. It is recited that the hydrolysis of potato material with 3% $H_2SO_4$ at 98 to 100° C. for 3.5 to 4 hours yielded a concentrate containing glucose, galactose and arabinose.

Kato, Y. et al. disclose an affinity chromatographic adsorbent for carbohydrate separation in Japanese Patent JP 06201671, Cosmo Sogo Kenkyusho Kk, Cosmo Oil Co Ltd, (published 22 Jul. 1994). It is recited that the affinity chromatographic adsorbent is a porous crosslinked copolymer containing alcoholic hydroxyl groups and lectin. It is also recited that the adsorbent is used in HPLC for the separation of carbohydrates, especially mannose and galactose.

Yamane, T. et al. disclose decomposition of raffinose by an enzymatic reaction applied in a factory-process in Japanese beet sugar factories in Sucr. Belge/Sugar Ind. Abstr. (1971), 90(7), 345-348. It is recited that raffinose is decomposed by $\alpha$-galactosidase into sucrose and galactose.

Dugal. H. et al. disclose enzymatic modification of locust bean and guar gums in IPPTA (1974), 11(1), 29-35. The effect of time, pH, temperature and enzyme and substrate concentration on the hydrolysis of locust bean gum and guar by $\alpha$-galactosidase isolated from sprouted guar seeds was studied and the hydrolyzed gums were characterized by X-ray diffraction and molecular weight determination. It is recited that the enzymatic hydrolysis of gums liberated galactose, arabinose and mannose. However, there is no xylose present in the substances used for the separation.

Non-published Finnish Patent Application 20012605, Danisco Sweeteners Oy discloses a method of recovering mannose from a solution derived from biomass by subjecting said solution to a chromatographic separation process using at least one chromatographic separation resin which is at least partly in $Ba^{2+}$ form and at least one chromatographic separation resin which is in other than $Ba^{2+}$ form. The latter resin is a cation exchange resin, where the cation is preferably $Ca^{2+}$. The starting biomass-derived solution typically contains mannose in admixture with other sugars, such as xylose, galactose, glucose, rhamnose, arabinose and fructose. Galactose is not recovered.

It appears from the above description of the prior art that it is known to prepare galactose-containing solutions from raw materials based on hemicellulose. However, it has been found difficult to produce pure crystalline D-galactose, because it is especially cumbersome to separate galactose from other sugars, especially from mannose and xylose, but also from arabinose and rhamnose, when the content of galactose in the starting solution is low.

This problem has now been solved in accordance with the present invention by providing a combination of chromatographic fractionation and crystallization to obtain pure crystalline galactose from plant-based hemicellulsose raw materials.

BRIEF DESCRIPTION OF THE INVENTION

It is an object of the present invention to provide a process for re-covering galactose from complex plant-based biomass-derived solutions so as to obtain pure galactose. The objects of the invention are achieved by a process, which is characterized by what is stated in the independent claims. The preferred embodiments of the invention are disclosed in the dependent claims.

The invention is based on a combination of chromatographic fractionation and crystallization to recover galactose from plant-based biomass-derived solutions which include galactose as an admixture with other closely-related sugars. The chromatographic fractionation provides a fraction enriched in galactose, which is then subjected to crystallization to obtain pure crystalline galactose. In one preferred embodiment of the invention, the chromatographic fractionation comprises successive separations using a strongly basic anion exchange resin in a bisulphite form. In another preferred embodiment of the invention, the chromatographic fractionation comprises separation with a strongly basic anion exchange resin and separation with a strongly acid cation exchange resin.

DEFINITIONS RELATING TO THE INVENTION

In the specification and throughout the examples and claims, the following definitions have been used:

SBA refers to a strongly basic anion exchange resin.

SAC refers to a strongly acid cation exchange resin.

DVB refers to divinylbenzene.

ACN refers to acetonitrile.

DS refers to a dry substance content measured by Karl Fischer titration, expressed as % by weight.

RDS refers to a refractometric dry substance content, expressed as % by weight.

SMB refers to simulated moving bed process.

"Galactose fraction" refers to a fraction enriched in galactose, obtained from chromatographic fractionation.

"Impurity profile" refers to the impurities and contents thereof in the final crystalline galactose product.

"Non-animal derived galactose" refers to non-dairy galactose and especially galactose, which is not based on a lactose hydrolyzate.

BRIEF DESCRIPTION OF THE DRAWINGS

The following drawings are illustrative embodiments of the invention and are not meant to limit the scope of the invention as defined in the claims in any way.

DETAILED DESCRIPTION OF THE INVENTION

Figure 1A:
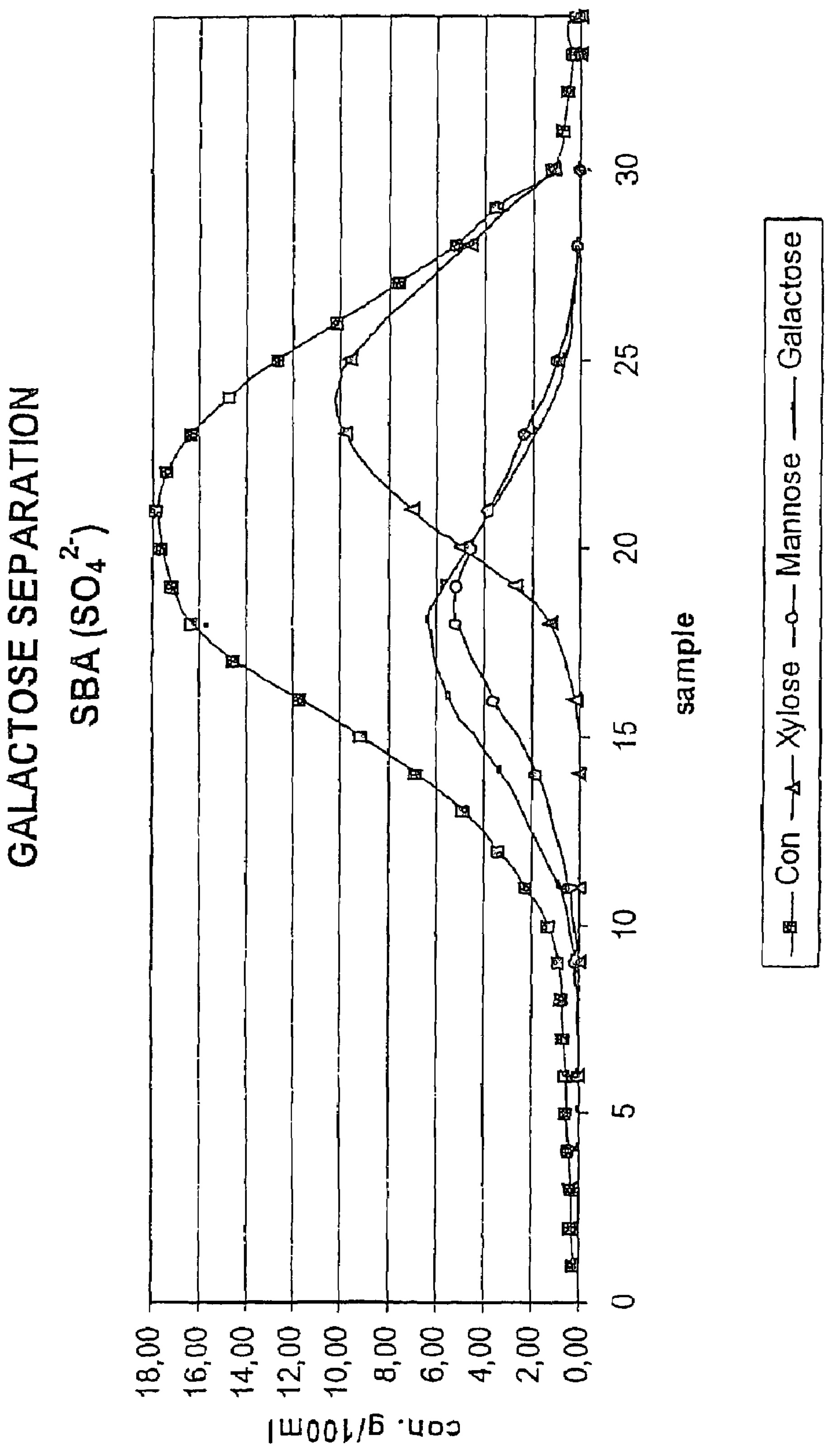
FIGS. 1A and 1B are graphical presentations of the separation profile obtained from Examples 1 and 2 (chromatographic fractionation of a solution based on sulphite spent liquor and containing mainly xylose, galactose and mannose using a strongly basic anion exchange resin in $SO_4^{2-}$ form).

The invention relates to a process of recovering galactose from a solution, which is derived from plant-based biomass. The process of the invention comprises subjecting said solution derived from plant-based biomass to one or more chromatographic fractionations, recovering at least one fraction enriched in galactose, subjecting said at least one fraction enriched in galactose to crystallization, and recovering a plant-based crystalline galactose product.

In one embodiment of the invention, said one or more chromatographic fractionations comprise one or more chromatographic fractionation steps using a column packing material selected from strongly basic anion exchange resins.

Said strongly basic anion exchange resin may be for instance in $SO_4^{2-}$ form, $SO_3^{2-}$ form, $HSO_3^-$ form or $CH_3COO^-$ form.

In one preferred embodiment of the invention, said strongly basic anion exchange resin is in $HSO_3^-$ form.

In one especially preferred embodiment of the invention, said one or more chromatographic fractionations comprise two successive chromatographic fractionation steps using a column filling material selected from strongly basic anion exchange resins in $HSO_3^-$ form.

In another embodiment of the invention, said one or more chromatographic fractionations comprise one or more chromatographic fractionation steps using a column filling material selected from strongly acid cation exchange resins.

Said strongly acid cation exchange resin may be in a monovalent metal form or in a divalent metal form. In a preferred embodiment of the invention, the resin is in $Ba^{2+}$, $Pb^{2+}$, $Ca^{2+}$ or $Sr^{2+}$ form.

However, even other chromatographic separation resins, for example weakly acid cation exchange resins are useful in the present invention used in acidic, neutral or slightly alkaline conditions for example for the separation of deoxysugars from galactose.

In one embodiment of the invention, said one or more chromatographic fractionations comprises one or more chromatographic fractionation steps using a column filling material selected from strongly basic anion exchange resins and one or more chromatographic fractionation steps using a column filling material selected from strongly acid cation exchange resins.

Said strongly basic anion exchange resin may be for instance in $SO_4^{2-}$ form, $SO_3^{2-}$ form, $HSO_3^-$ form or $CH_3COO^-$ form.

Said strongly acid cation exchange resin may be in a monovalent metal form or in a divalent metal form. In a preferred embodiment of the invention, the resin is in $Ba^{2+}$, $Pb^{2+}$, $Ca^{2+}$ or $Sr^{2+}$ form.

Said strongly basic anion exchange resins and said strongly acid cation exchange resins may have a styrene or acrylic skeleton. In a preferred embodiment of the invention, the resin is a polystyrene-co-divinylbenzene resin. Other alkenylaromatic polymer resins like those based on monomers like alkyl-substituted styrene or mixtures thereof can also be applied. The resin may also be crosslinked with other suitable aromatic crosslinking monomers, such as divinyltoluene, divinylxylene, divinylnaphtalene, divinylbenzene, or with aliphatic crosslinking monomers, such as isoprene, ethylene glycol diacrylate, ethylene glycol dimethacrylate, N,N'-methylene bisacrylamide or mixtures thereof. The cross-linking degree of the resins is typically from about 1 to about 20%, preferably from about 3 to about 8% of the cross-linking agent, such as divinyl benzene. The average particle size of the resin is normally 10 to 2000 μm, preferably 100 to 400 μm.

Said strongly acid cation exchange resin is preferably a sulphonated polystyrene-co-divinylbenzene resin.

In a preferred embodiment of the invention, the resins are gel-type resins.

Manufacturers of the resins are for example Finex, Dow, Bayer and Rohm & Haas.

In the chromatographic fractionation operation, the cations/anions of the resin are preferably in substantial equilibrium with the cations/anions of the mobile phase of the system.

The eluent used in the chromatographic fractionation is preferably water, but even solutions of salts and water are useful. Furthermore, alcohols, such as ethanol, and mixtures of water and alcohol, such as a mixture of water and ethanol are useful eluents.

The temperature of the chromatographic fractionation is typically in the range of 20 to 90° C., preferably 40 to 65° C. The pH of the solution to be fractionated is typically in the range of 2 to 9.

The chromatographic fractionation may be carried out as a batch process or a simulated moving bed process (SMB process). The SMB process is preferably carried out as a sequential or continuous process.

In the simulated moving bed process, the chromatographic fractionation is typically carried out using 3 to 14 columns connected in series. The columns are connected with pipelines. Flow rate in the columns is typically 0.5 to 10 $m^3/(hm^2)$ of the cross-sectional area of the column. Columns are filled with a column packing material selected from the resins described above. The columns are provided with feed lines and product lines so that the feed solution and the eluent can be fed into the columns and the product fractions collected from the columns. The product lines are provided with on-line instruments so that the quality/quantity of the production flows can be monitored during operation.

During the chromatographic SMB separation, the feed solution is circulated through the columns by means of pumps. Eluent is added, and the galactose fraction, other optional product fractions and residual fractions are collected from the columns.

Before the chromatographic fractionation, the feed solution may be subjected to one or more pretreatment steps selected from softening by ion-exchange treatment or carbonation, dilution, concentration e.g. by evaporation, pH adjustment and filtration, for example. Before feeding into the columns, the feed solution and the eluent are heated to the fractionation temperature described above (for instance in the range of 50 to 85° C.).

The chromatographic fractionation provides a galactose fraction where galactose is in a solution form. The galactose fraction obtained from the chromatographic fractionation has a typical purity of more than 38% galactose on RDS. In one typical embodiment of the invention, the chromatographic fractionation provides a galactose fraction having a purity of 38% to 95% galactose on RDS. The yield of galactose in the chromatographic fractionation is typically 35 to 95%.

The galactose fraction obtained from the chromatographic fractionation typically includes further sugars selected from xylose, arabinose, rhamnose and mannose as impurities. The amount of xylose is typically in the range of 1 to 20% and the amount of mannose is typically in the range of 2 to 40% on RDS.

To improve the yield of the chromatographic fractionation, recycle fractions of the chromatographic fractionation can also be used.

The chromatographic fractionation method of the invention may further comprise one or more purification steps selected from membrane filtration (microfiltration, ultrafiltration or nanofiltration), ion exchange, evaporation, post hydrolysis and filtration. These purification steps may be carried out before, after or between said chromatographic fractionation steps.

The galactose fraction obtained from the chromatographic fractionation is further subjected to crystallization to obtain a crystalline galactose product. The crystallization is typically carried out using a solvent selected from water, alcohol, such as ethanol, and a mixture of water and alcohol, such as ethanol. In a preferred embodiment of the invention, the crystallization is carried out with water.

The crystallization is carried out by evaporating the galactose solution obtained from the chromatographic fractionation to an appropriate dry substance content (e.g. to an RDS of about 70 to 80%). The galactose solution may be seeded with galactose seed crystals. The seeds, if used, are suspended in a crystallization solvent, which may be water, an alcohol, such as ethanol, or a mixture thereof. A typical crystallization solvent is water. After cooling the crystallization mass, a crystallization solvent, like ethanol may beadded. The crystallization mass may then be allowed to stand for a period of time, preferably from 1 to 6 days, typically at room temperature, whereafter the crystals are filtered off. The filtration cake is washed with the crystallization solvent. Galactose crystals with a high purity are obtained.

The crystallization provides crystalline galactose having a purity of over 90%, preferably over 95% and more preferably over 98% and most preferably more than 99.5% on DS. The crystalline galactose product can be further purified using recrystallization steps even to the purity up to 99.9%.

The crystallization may be carried out from a galactose solution having a purity of more than 38% galactose on RDS. In one typical embodiment of the invention, the crystallization is carried out from a solution having a purity of 38 to 95% galactose on RDS. The galactose solution used for the crystallization typically refers to the galactose fraction obtained from the chromatographic fractionation.

In one embodiment of the invention, galactose may be crystallized with one crystallization step from a purity of at least 50% on RDS to obtain crystalline galactose having a purity of more than 98% on DS.

The crystallization typically provides crystalline galactose having a maximum content of glucose of 0.50% on DS, preferably a maximum content of glucose of 0.30% on DS.

The crystallization also provides crystalline galactose having an impurity profile comprising at least one sugar selected from xylose, arabinose, rhamnose and mannose. In one embodiment of the invention, the crystallization provides crystalline galactose, wherein the impurity profile comprises at least one of said sugars in an amount of 0.03% on DS or more. In another embodiment of the invention, the crystallization provides crystalline galactose, where the impurity profile comprises arabinose and/or mannose in an amount of 0.03% on DS or more. In a further embodiment of the invention, the crystallization provides crystalline galactose having an impurity profile comprising at least one of said sugars selected from xylose, arabinose, rhamnose and mannose in an amount of 0.10% on DS or more.

Said galactose typically refers to D-galactose. Furthermore, glucose refers to D-glucose, xylose refers to D-xylose, arabinose refers to L-arabinose, mannose refers to D-mannose and rhamnose refers to L-rhamnose.

The process of the invention may also comprise one or more purification steps selected from membrane filtration, ion exchange, evaporation and filtration carried out before, after or between said chromatographic fractionation steps.

The process of the invention may also comprise partial recovery of other sugars, such as xylose, mannose and optionally rhamnose. The partial recovery of the other sugars are typically carried out before the separation of galactose.

The process of the invention may further comprise one or more crystallization steps between said chromatographic fractionation steps. Said one or more crystallization steps may comprise for example the precipitation crystallization of xylose. Said precipitation crystallization of xylose is typically carried out between said chromatographic fractionation with a strongly basic anion exchange resin and said chromatographic fractionation with a strongly acid cation exchange resin.

The starting material for the recovery of galactose is typically a plant-based mixture containing carbohydrates, such as monosaccharides. In a typical embodiment of the invention, said monosaccharides mainly comprise xylose, galactose, mannose, arabinose, rhamnose and optionally glucose. The mixture may also contain mono- and disaccharides and higher saccharides. Especially, the present invention may be applied to the production of galactose from solutions containing considerable amounts of xylose and/or mannose together with galactose.

The starting material for the recovery of galactose in accordance with the present invention is derived from plant-based biomass, typically from hemicellulose-containing plant-based material, such as wood material selected softwood or hardwood, grain straw or hulls, corn husks, corn cops, corn fibers, bagasse and sugar beet. Softwood material is especially rich in galactose. Hemicellulose-containing biomass derived from softwood, such as spruce or pine, is thus especially preferred for use as starting material in the present invention.

As other suitable starting materials can be mentioned exudate gums, such as gum arabic, gum tragacanth and gum ghatti, for example.

The starting material for the recovery of galactose is typically a hydrolysate of the above-described hemicellulose-containing biomass. The hydrolysate has been typically obtained from mild acid hydrolysis or enzymatic hydrolysis of the biomass. Hexoses, such as glucose may optionally be removed by fermentation. In a preferred embodiment of the invention, the starting material is a plant-based hemicellulose hydrolysate. In another preferred embodiment of the invention, the starting material is a plant-based hemicellulose hydrolysate containing galactose and further sugars selected from xylose. In another preferred embodiment of the invention, the starting material is a plant-based hemicellulose hydrolysate containing galactose and further sugars selected from xylose, arabinose and mannose. Also hemicellulose concentrates and extracts, such as alkaline extracts are useful starting materials in the process of the invention.

The biomass hydrolysate for the recovery of galactose in accordance with the present invention is typically a spent liquor obtained from a pulping process. The spent liquor is especially a spent sulphite pulping liquor, which may be obtained by acid, basic or neutral sulphite pulping, preferably acid sulphite pulping.

A typical spent liquor useful in the present invention is a spent liquor, which is preferably obtained from acid sulphite pulping. The spent liquor may be obtained directly from sulphite pulping. It may also a concentrated sulphite pulping liquor or a side-relief obtained from sulphite cooking. It may also be a galactose-containing fraction chromatographically obtained from a sulphite pulping liquor.

The starting solution containing galactose may be e.g. a spent sulphite pulping liquor recovered after the separation of the main part of xylose.

In one embodiment of the invention, the starting material may be a side stream obtained after the separation of the main part of mannose, said side stream containing galactose and rests of mannose and xylose. The mannose separation refers to a process of recovering mannose from sulphite spent liquor after the recovery of the main part of xylose and rhamnose.

Said solution derived from plant-based biomass typically contains galactose and one or more further sugars selected from xylose, arabinose, mannose and rhamnose. In one embodiment of the invention, said solution derived from plant-based biomass contains galactose and one or more further sugars selected from arabinose and mannose.

Said solution used for the recovery of galactose is typically a plantbased hemicellulose hydrolysate, which typically contains xylose, galactose and mannose in approximately equal amounts. However, hardwood hemicellulose hydrolysate typically contains more xylose than galactose or mannose. In plant-based hemicellulose hydrolysate, the galactose content is typically at minimum 5%, preferably 20% and most preferably 40%. The mannose content is typically 40% or more, preferably 20% and most preferably 5% or more. The xylose content is typically 40% or more, preferably 20% or more and most preferably 5% or more.

The invention also relates to plant-based crystalline D-galactose obtained by the process of the invention. Specifically, the invention relates to non-animal derived crystalline D-galactose. Non-animal derived D-galactose refers to non-dairy D-galactose and especially D-galactose which is not based on a lactose hydrolyzate.

Furthermore, the invention relates to plant-based crystalline D-galactose having a melting point in the range of 163 to 169° C. and a purity of more than 90%. In one preferred embodiment of the invention, the invention relates to crystalline D-galactose derived from plant-based hemicellulose-containing material, which may be wood selected from softwood or hardwood. The invention also relates to plant-based crystalline galactose having a purity of more than 90% on DS, more preferably more than 95% on DS, even more preferably more than 98% on DS and most preferably more than 99.5% on DS.

The invention also relates to plant-based crystalline D-galactose having a maximum content of D-glucose of 0.50% on DS, preferably a maximum content of D-glucose of 0.30% DS.

Furthermore, the invention relates to non-animal derived crystalline D-galactose having an impurity profile comprising at least one sugar selected from D-xylose, L-arabinose, D-mannose and L-rhamnose. In one embodiment of this aspect of the invention, the impurity profile comprises at least one of said sugars in an amount of 0.03% on DS or more (at least 0.03% on DS). In another embodiment of this aspect of the invention, the impurity profile comprises L-arabinose and/or D-mannose in an amount of 0.03% on DS or more. In a further embodiment of this aspect of the invention, the impurity profile comprises at least one of said sugars selected from D-xylose, L-arabinose, D-mannose and L-rhamnose in an amount of 0.10% on DS or more (at least 0.10% on DS).

The invention also relates to crystalline non-animal derived D-galactose, which has an impurity profile comprising D-glucose in an amount of less than 0.50%, preferably less than 0.30% on DS.

The invention also relates to crystalline non-animal derived D-galactose, which has an impurity profile comprising lactose in an amount of less than 0.10%, preferably less than 0.03% on DS.

Furthermore, the invention relates to non-animal derived D-galactose, which has an impurity profile comprising D-glucose in an amount of less than 0.50% on DS, lactose in an amount of less than 0.10% on DS and at least one further sugar selected from D-xylose, L-arabinose, D-mannose and L-rhamnose. In one embodiment of this aspect of the invention, the impurity profile comprises at least one of said sugars selected from D-xylose, L-arabinose, D-mannose, L-rhamnose and D-lyxose in an amount of 0.03% on DS or more, typically L-arabinose in an amount of 0.03% or more and/or D-mannose in an amount of 0.03% on DS or more. In another embodiment of the invention, the impurity profile comprises at least one of said sugars in an amount of 0.10% on DS or more. In a further embodiment of the invention, the impurity profile comprises D-glucose in an amount of less than 0.30% and lactose in an amount of less than 0.03% on DS.

In the crystalline D-galactose of the invention, the sum of individual sugar impurities selected from D-xylose, L-arabinose, D-mannose and L-rhamnose may be up to 10% on DS, depending on the purity of the galactose product. The upper limit for each individual sugar impurity selected from D-xylose, L-arabinose, D-mannose and L-rhamnose may be up to 5% on DS, preferably up to 2% on DS, more preferably up to 1% on DS and even more preferably up to 0.5% on DS, depending on the purity of the galactose product. The lower limit for said sugar impurities is that defined in the claims, i.e. typically 0.03% on DS. However, the lower limit for example for D-xylose may be even as low as zero, depending on the purity level of the galactose product.

The invention also relates to a crystalline galactose intermediate product having a purity of more than 70% galactose on DS and including further sugars selected from xylose, arabinose, rhamnose and mannose in an amount of 2 to 10% on DS.

The crystalline D-galactose of the invention is preferably plant-based D-galactose, which is derived from plant-based biomass, such as a plant-based hemicellulose hydrolysate or a plant-based hemicellulose extract. In one preferred embodiment of the invention, the crystalline D-galactose of the invention is derived from wood.

The crystalline D-galactose of the invention is further characterized by a melting point in the range of 163 to 169° C.

The crystalline D-galactose of the invention which has the impurity profile described above is preferably obtained from plant-based biomass by a combination of chromatographic separation and crystallization described above.

The invention also relates to the use of the crystalline D-galactose of the invention in pharmaceuticals and foodstuffs. Especially, the invention relates to the use of the plant-based crystalline D-galactose as pharmaceutical intermediates and as ingredients in pharmaceuticals, for example as a stabilizer in intravenous solutions for medical use.

The invention also relates to the use of the crystalline galactose of the invention as an intermediate for the preparation of pharmaceutically active ingredients, for example 2-deoxy-2-ribose, L-deoxythymidine, D-tagatose, D-fucose and potassium D-lyxonate.

The invention also relates to the use of the plant-based crystalline D-galactose of the invention as food ingredients in foodstuffs, for example in sports drinks as a potential energy source.

Furthermore, the invention relates to the use of the plant-based crystalline D-galactose of the invention as an ingredient in cell culture media, where D-galactose is useful as a nutrient or an inducer in the fermentation.

The invention also encompasses pharmaceuticals, foodstuffs and cell culture media comprising the crystalline D-galactose of the invention.

The following examples represent illustrative embodiments of the invention without limiting the invention in any way.

Example 1

Chromatographic Separation of a Galactose-Containing Solution with a Strongly Basic Anion Exchange Resin (SBA Resin) in $SO_4^{2-}$ Form The starting liquor used for the separation of galactose was a galactose-containing side stream separated from calcium sulphite spent liquor used for the recovery of xylose. Birch had been used as the raw material for the sulphite pulping.

The solution containing galactose was subjected to chromatographic separation. The separation was performed in a pilot scale chromatographic separation column as a batch process. The column with a diameter of 0.225 m was filled with a strongly basic anion exchange resin (Finex As 532 GC, 3.5% DVB). The height of the resin bed was 5.3 m. The average particle size of the resin was 0.35 mm. The resin was regenerated into sulphate ($SO_4^{2-}$)-form. The temperature of the column and feed solution and eluent water was 65° C. The flow rate in the column was adjusted to 25 l/h. The pH of the feed solution was 2.6.

The feed solution had the following composition on DS:

Galactose: 23%

Xylose: 40%

Mannose: 20%

Others: 17%.

The chromatographic separation was carried out as follows:

Step 1: The dry substance of the feed solution was adjusted to 30 g dry substance in 100 g solution according to the refractive index (RI) of the solution.

Step 2: 12.5 l of preheated feed solution was pumped to the top of the resin bed.

Step 3: The feed solution was eluted downwards in the column by feeding preheated ion-exchanged water to the top of the column.

Step 4: 50 ml samples of the out-coming solution were collected at 5 min intervals. The composition of the samples was analyzed with HPLC (amino column), and a mixture of water and ACN was used as the eluent.

The separation profile is presented in FIG. 1A and fraction data in Table 1. It can be seen that xylose starts eluting later than other sugars. Thus with a sulphate-form strongly basic anion exchange resin galactose can be separated from xylose. The pH of the effluent (e.g. the out-coming solution) was between 3.3-3.6.

TABLE 1

Fraction data from a chromatographic separation test with an SBA resin in $SO_4^{2-}$ form

| | Galactose fraction | Xylose fraction |
|---|---|---|
| Volume, I | 22 | 16 |
| Concentration, g/100 ml | 8.8 | 8.2 |
| Galactose, % on DS | 40.6 | 6.8 |
| Mannose, % on DS | 29.5 | 8.5 |
| Xylose, % on DS | 9.8 | 77.8 |
| Galactose yield, % | 78.3 | 8.9 |
| Mannose yield, % | 70.1 | 13.8 |
| Xylose yield, % | 12.5 | 67.8 |

The yield is calculated from all the components eluted from the column.

Example 2

Chromatographic Separation of a Galactose-Containing Solution with a Strongly Basic Anion Exchange Resin (SBA Resin) in $S_4^{2-}$ Form in an Industrial Scale The starting liquor used for the separation was a galactose-containing side stream separated from calcium sulphite spent liquor used for the recovery of xylose. Birch had been used as the raw material for the sulphite pulping.

The solution containing galactose was subjected to chromatographic separation. The separation was performed in a pilot scale chromatographic separation column as a batch process. The column with a diameter of 1.0 m was filled with a strongly basic anion exchange resin (Finex AS 510 GC, 4.0% DVB). The height of the resin bed was approximately 5.8 m. The average particle size of the resin was 0.27 mm. The resin was regenerated into sulphate ($SO_4^{2-}$)-form. The temperature of the column and feed solution and eluent water was 57° C. The flow rate in the column was adjusted to 495 l/h. The pH of the feed solution was 2.6.

The feed solution had the following composition on DS:

Galactose: 24%

Xylose: 44%

Mannose: 10%

Arabinose: 1.5%

Others: 20.5%.

The chromatographic separation was carried out as follows:

Step 1: The dry substance of the feed solution was adjusted to 30 g dry substance in 100 g solution according to the refractive index (RI) of the solution.

Step 2: 270 l of preheated feed solution was pumped to the top of the resin bed.

Step 3: The feed solution was eluted downwards in the column by feeding preheated ion-exchanged water to the top of the column.

Step 4: Samples of the out-coming solution were collected at 5 min intervals. The composition of the samples was analyzed with HPLC (amino column), and a mixture of water and ACN was used as the eluent.

Figure 1B:
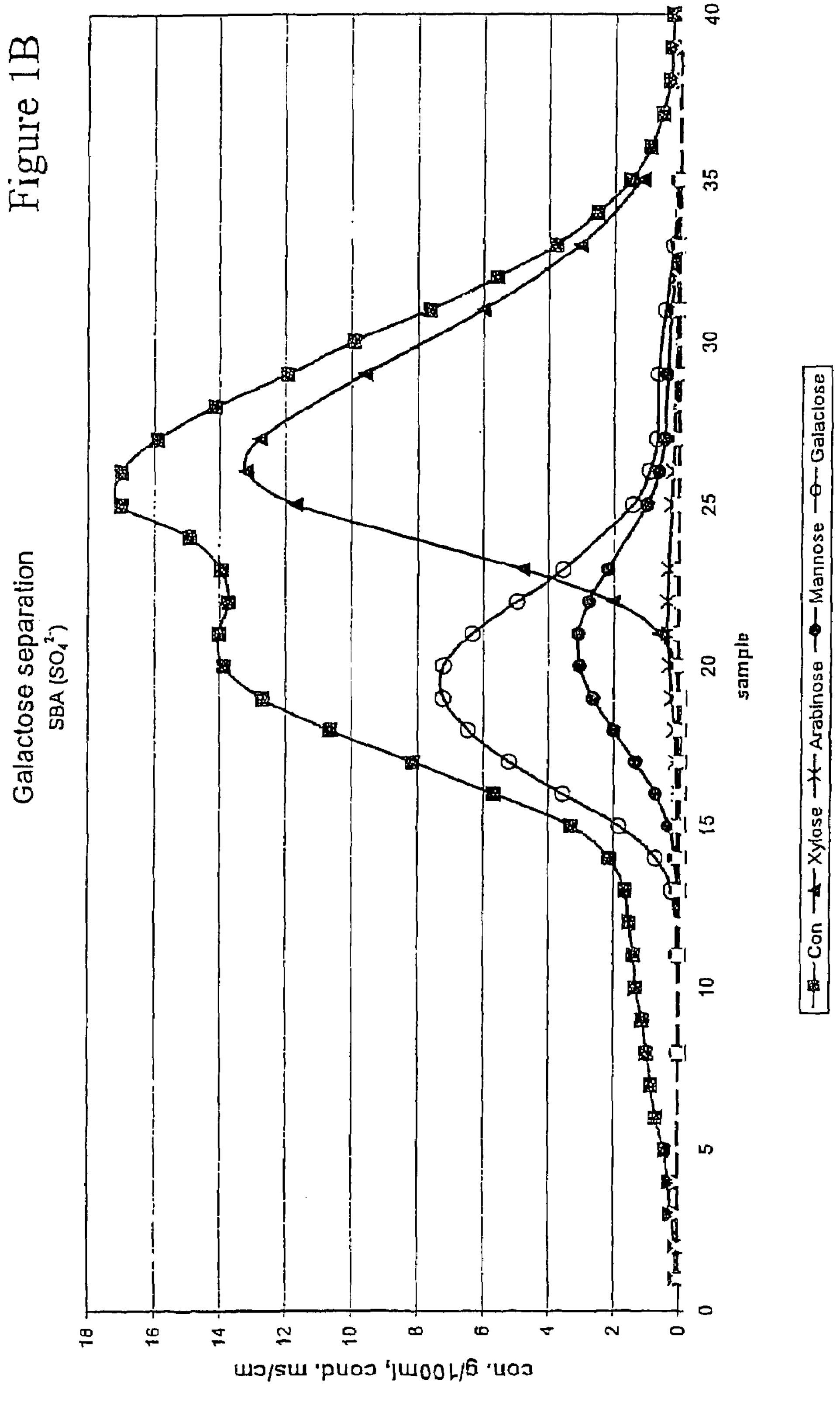

The separation profile is presented in FIG. 1B and fraction data in Table 2. It can be seen that xylose starts eluting later than other sugars. Thus with a sulphate-form strongly basic anion exchange resin galactose can be separated from xylose. The pH of the effluent (e.g. the out-coming solution) was between 3.3-3.6.

TABLE 2

Fraction data from a chromatographic separation test with an SBA resin in $SO_4^{2-}$ form in an industrial scale

| | Galactose fraction | Xylose fraction |
|---|---|---|
| Volume, I | 247 | 594 |
| Concentration, g/100 ml | 8.3 | 8.4 |
| Galactose, % on RDS | 58.2 | 6.5 |
| Mannose, % on RDS | 17.8 | 4.7 |
| Xylose, % on RDS | 0.2 | 78.2 |
| Glucose, % on RDS | 7.1 | 5.2 |
| Galactose yield, % | 53.5 | 14.6 |
| Mannose yield, % | 38.1 | 24.7 |
| Xylose yield, % | 0.1 | 94.4 |
| Glucose yield, % | 22.2 | 39.9 |

The yield is calculated from all the components eluted from the column.

Example 3

Chromatographic Separation of a Galactose-Containing Solution with a Strongly Basic Anion Exchange Resin (SBA Resin) in $S_4^{2-}$ Form The starting liquor used for the separation was a galactose-containing side stream separated from calcium sulphite spent liquor used for the recovery of xylose. Birch had been used as the raw material for the sulphite pulping.

The solution containing galactose was subjected to chromatographic separation. The separation was performed in a plant scale chromatographic separation column as a batch process. The column with a diameter of 2.74 m was filled with a strongly basic anion exchange resin (Finex AS 510 GC, 4.0% DVB). The height of the resin bed was approximately 6.4 m. The average particle size of the resin was 0.27 mm. The resin was regenerated into ($SO_4^{2-}$)-form. The temperature of the column and feed solution and eluent water was 60° C. The flow rate in the column was adjusted to 770 l/h. The pH of the feed solution was 2.5-2.8.

The feed solution had the following composition on DS:

Galactose: 23%

Xylose: 42%

Mannose: 8.5%

Glucose: 7%

Others: 19.5%.

The chromatographic separation was carried out as follows:

Step 1: The dry substance of the feed solution was adjusted to 39 g dry substance in 100 g solution according to the refractive index (RI) of the solution.

Step 2: 1890 l of preheated feed solution was pumped to the top of the resin bed.

Step 3: The feed solution was eluted downwards in the column by feeding preheated ion-exchanged water to the top of the column.

Step 4: Samples of the out-coming solution were collected at 5 min intervals. The composition of the samples was analyzed with HPLC (amino column), and a mixture of water and ACN was used as the eluent.

The fraction data is presented in Table 3. It can be seen that xylose starts eluting later than other sugars. Thus with a sulphate-form strongly basic anion exchange resin galactose can be separated from xylose. The pH of the effluent (e.g. the out-coming solution) was between 3.3-3.6.

TABLE 3

Fraction data from a chromatographic separation test with an SBA resin in ($SO_4^{2-}$) form

| | Xylose fraction | Galactose fraction |
|---|---|---|
| Volume, I | 4895 | 2082 |
| Concentration, g/100 ml | 8.53 | 10.0 |
| Galactose, % on RDS | 8.4 | 57.2 |
| Mannose, % on RDS | 5.4 | 17.5 |
| Xylose, % on RDS | 65.8 | 0.7 |
| Glucose, % on RDS | 4.7 | 11.2 |
| Galactose yield, % | 16.2 | 54.9 |
| Mannose yield, % | 24.9 | 40.3 |
| Xylose yield, % | 81.4 | 0.4 |
| Glucose yield, % | 29.3 | 34.8 |

Example 4

Chromatographic Separation of a Galactose-Containing Solution with a Strongly Basic Anion Exchange Resin in $SO_3^{2-}$ Form A solution containing xylose, mannose, galactose, glucose and arabinose was subjected to chromatographic separation. The separation was performed in a preparative scale chromatographic separation column as a batch process. The column with a diameter of 0.044 m was filled with a strongly basic anion exchange resin (Zerolite FF, 7-9% DVB). The height of the resin bed was approximately 84 cm. The average particle size of the resin was 0.13 mm. The resin was regenerated into sulphite ($SO_3^{2-}$)-form. The temperature of the column and feed solution and eluent water was 55° C. The flow rate in the column was adjusted to 3 ml/min.

The feed solution was a synthetic mixture having the following composition on DS (corresponding approximately to the composition of the main sugar components in hardwood hemicellulose hydrolyzate):

Galactose: 10%

Xylose: 60%

Mannose: 10%

Glucose: 10%

Arabinose: 10%.

The chromatographic separation was carried out as follows:

Step 1: The dry substance of the feed solution was adjusted to 40 g dry substance in 100 ml solution.

Step 2: 50 ml of feed solution was fed to the top of the resin bed.

Step 3: The feed solution was eluted downwards in the column by feeding preheated ion-exchanged water to the top of the column.

Step 4: The out-coming solution was collected as 15 ml samples. The composition of the samples was analyzed as alditol acetate derivatives with GC equipment; using a packed column and FID-detection.

Figure 2:
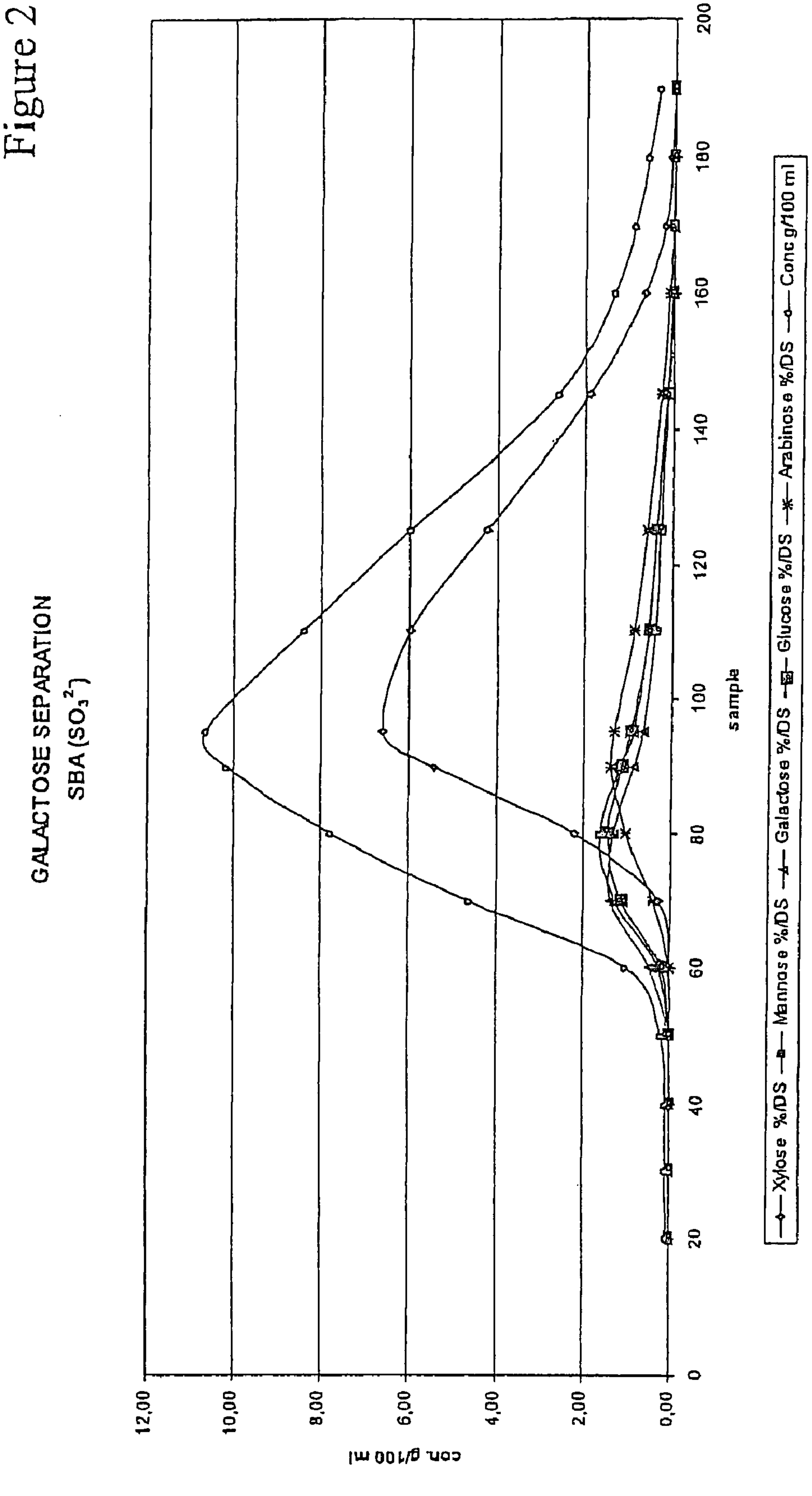
FIG. 2 is a graphical presentation of the separation profile obtained from Example 4 (chromatographic fractionation of a solution containing mainly xylose, mannose, galactose, glucose and arabinose using a strongly basic anion exchange resin in $SO_3^{2-}$ form).

The separation profile is presented in FIG. 2. Mannose, galactose and glucose are eluting from the column before xylose. Arabinose is eluting after mannose, galactose and glucose, but before xylose. Thus with a sulphiteform strongly basic anion exchange resin galactose can be separated well from xylose.

Example 5

Chromatographic Separation of a Glactose-Containing Solution with a Strongly Basic Anion Exchange Resin in $HSO_3^-$ Form A solution containing xylose, mannose, galactose and glucose was subjected to chromatographic separation. The separation was performed in a preparative scale chromatographic separation column as a batch process. The column with a diameter of 0.044 m was filled with a strongly basic anion exchange resin (Zerolite IP, 3-4% DVB). The height of the resin bed was approximately 20 cm. The average particle size of the resin was 0.13 mm. The resin was regenerated into bisulphite ($HSO_3^-$)-form. The temperature of the column and feed solution and eluent water was 50° C. The flow rate in the column was adjusted to 1.4-1.6 ml/min.

The feed solution was a synthetic mixture containing 68% xylose, 8% mannose, 8% galactose, 8% glucose as well as other sugars (corresponding approximately to the composition of hardwood hemicellulose hydrolyzate).

The chromatographic separation was carried out as follows:

Step 1: The dry substance of the feed solution was adjusted to 35 g dry substance in 100 g solution.

Step 2: 65 ml of feed solution was fed to the top of the resin bed.

Step 3: The feed solution was eluted downwards in the column by feeding preheated ion-exchanged water to the top of the column.

Step 4: The out-coming solution was collected as 10.5 ml samples. The composition of the samples was analyzed as silylation derivatives with GC equipment; using a packed column and FID-detection.

Figure 3:
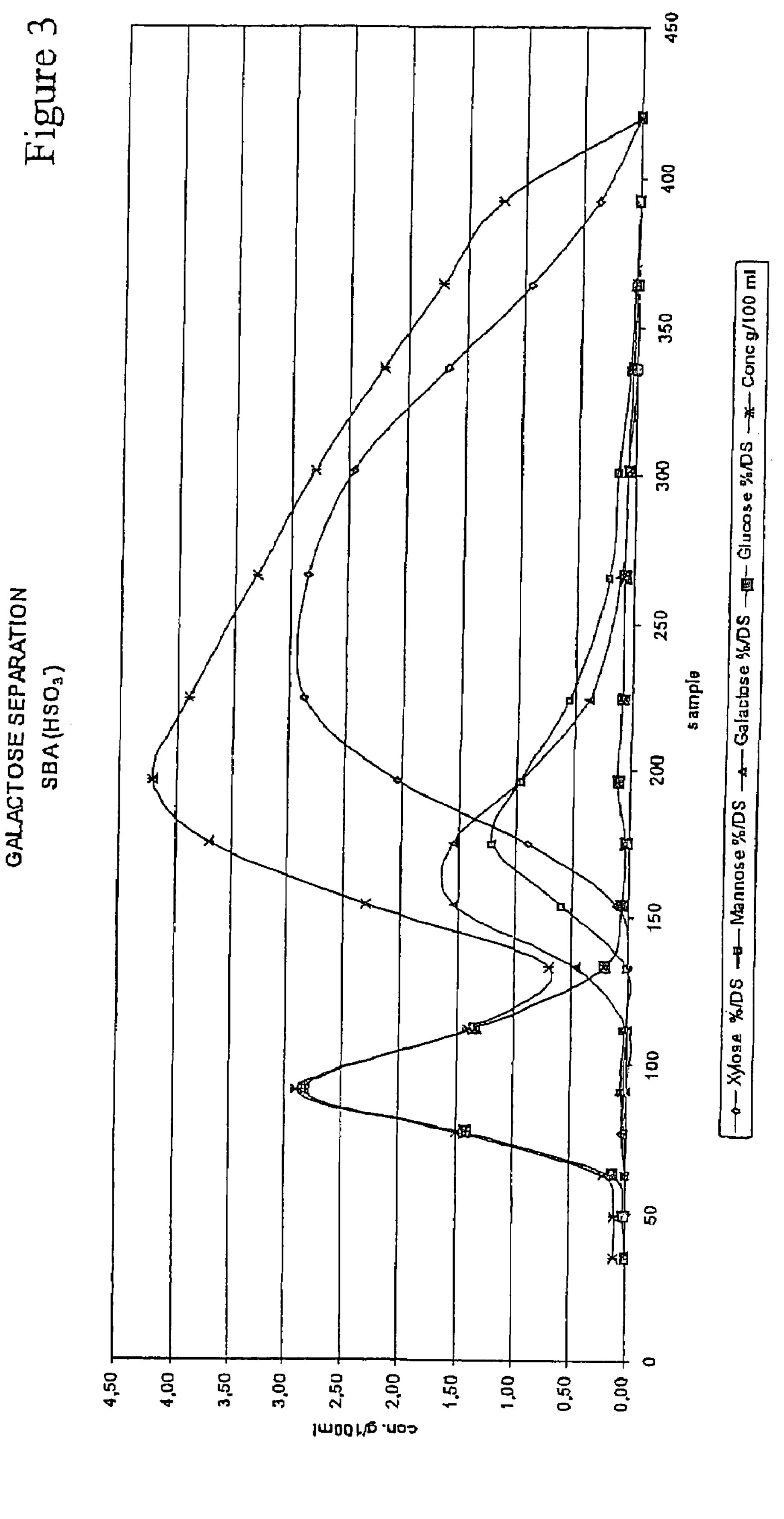
FIG. 3 is a graphical presentation of the separation profile obtained from Example 5 (chromatographic fractionation of a solution containing mainly xylose, mannose, galactose and glucose using a strongly basic anion exchange resin in $HSO_3^-$ form).

The separation profile is presented in FIG. 3. Glucose elutes first and then mannose and galactose are eluting from the column before xylose. Thus with a bisulphite strongly basic anion exchange resin galactose can be separated well from xylose and glucose.

Example 6

Chromatographic Separation of a Galactose-Containing Solution with a Strongly Basic Anion Exchange Resin in $CH_3COO^-$ Form A solution containing xylose, mannose, galactose, glucose and arabinose was subjected to a chromatographic separation. The separation was performed in a preparative scale chromatographic separation column as a batch process. The column with a diameter of 0.044 m was filled with a strongly basic anion exchange resin (Zerolite FF, 3-5% DVB). The height of the resin bed was approximately 84 cm. The average particle size of the resin was 0.13 mm. The resin was regenerated into acetate ($CH_3COO^-$)-form. The temperature of the column and feed solution and eluent water was 55° C. The flow rate in the column was adjusted to 4.1 ml/min.

The feed solution was a synthetic mixture having the following composition on DS (corresponding approximately to the composition of hardwood hemicellulose hydrolysate):

Galactose: 10%
Xylose: 60%
Mannose: 10%
Glucose: 10%
Arabinose: 10%.

The chromatographic separation was carried out as follows:

Step 1: The dry substance of the feed solution was adjusted to 38.8 g dry substance in 100 ml solution.

Step 2: 51.5 ml of feed solution was fed to the top of the resin bed.

Step 3: The feed solution was eluted downwards in the column by feeding preheated ion-exchanged water to the top of the column.

Step 4: The out-coming solution was collected as 20.5 ml samples. The composition of the samples was analyzed as alditol acetate derivatives with GC equipment; using a packed column and FID-detection.

Figure 4:
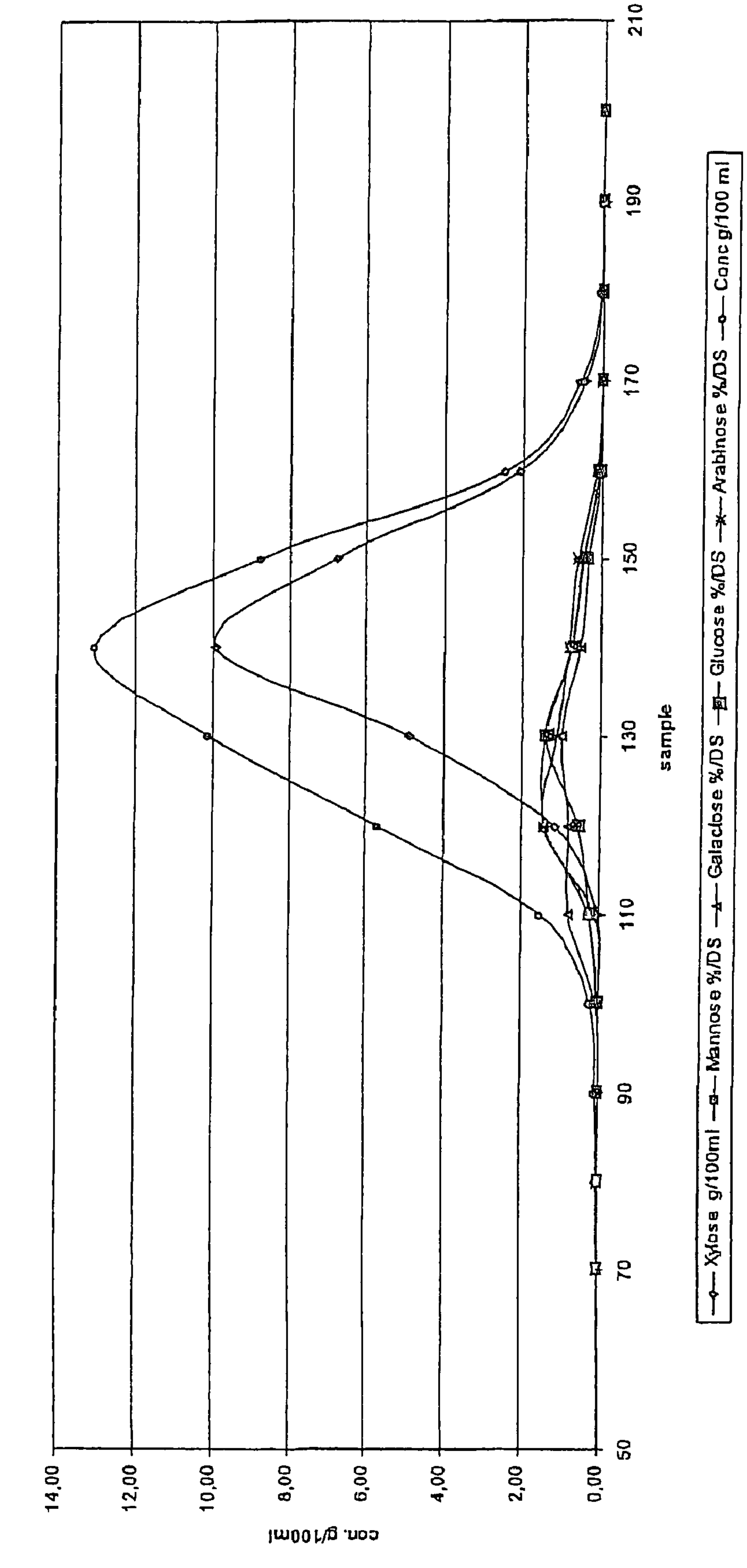
FIG. 4 is a graphical presentation of the separation profile obtained from Example 6 (chromatographic fractionation of a solution containing mainly xylose, mannose, galactose, glucose and arabinose using a strongly basic anion exchange resin in $CH_3COO^-$ form).

The separation profile is presented in FIG. 4. Galactose elutes first and then mannose, glucose and arabinose are eluting from the column before xylose. Thus with an acetate-form strongly basic anion exchange resin galactose can be separated well from xylose.

Example 7

Chromatographic Separation of a Galactose-Containing Solution with a Strongly Acid Cation Exchange Resin in $Ba^{2+}$ Form A solution containing galactose was subjected to chromatographic separation. The separation was performed in a plant scale chromatographic separation column as a batch process. The column with a diameter of 2.74 m was filled with a strongly acid cation exchange resin (Finex CS 08 GC, 4.0% DVB) that was in $Ba^{2+}$ form. The height of the resin bed was approximately 6.8 m. The average particle size of the resin was 0.3 mm. The temperature of the column and feed solution and eluent water was 68 to 70° C. The flow rate in the column was adjusted to 0.69 m/h. The pH of the feed solution was approximately 3.0.

The feed solution had the following composition on DS:

Galactose: 17%
Xylose: 29%
Mannose: 22%
Others: 32%.

The chromatographic separation was carried out as follows:

Step 1: The dry substance of the feed solution was adjusted to 35 g dry substance in 100 g solution according to the refractive index (RI) of the solution.

Step 2: 1890 l of preheated feed solution was pumped to the top of the resin bed.

Step 3: The feed solution was eluted downwards in the column by feeding preheated ion-exchanged water to the top of the column.

Step 4: Samples of the out-coming solution were collected at 5 min intervals. The composition of the samples was analyzed with HPLC (amino column), and a mixture of water and ACN was used as the eluent.

Figure 5:
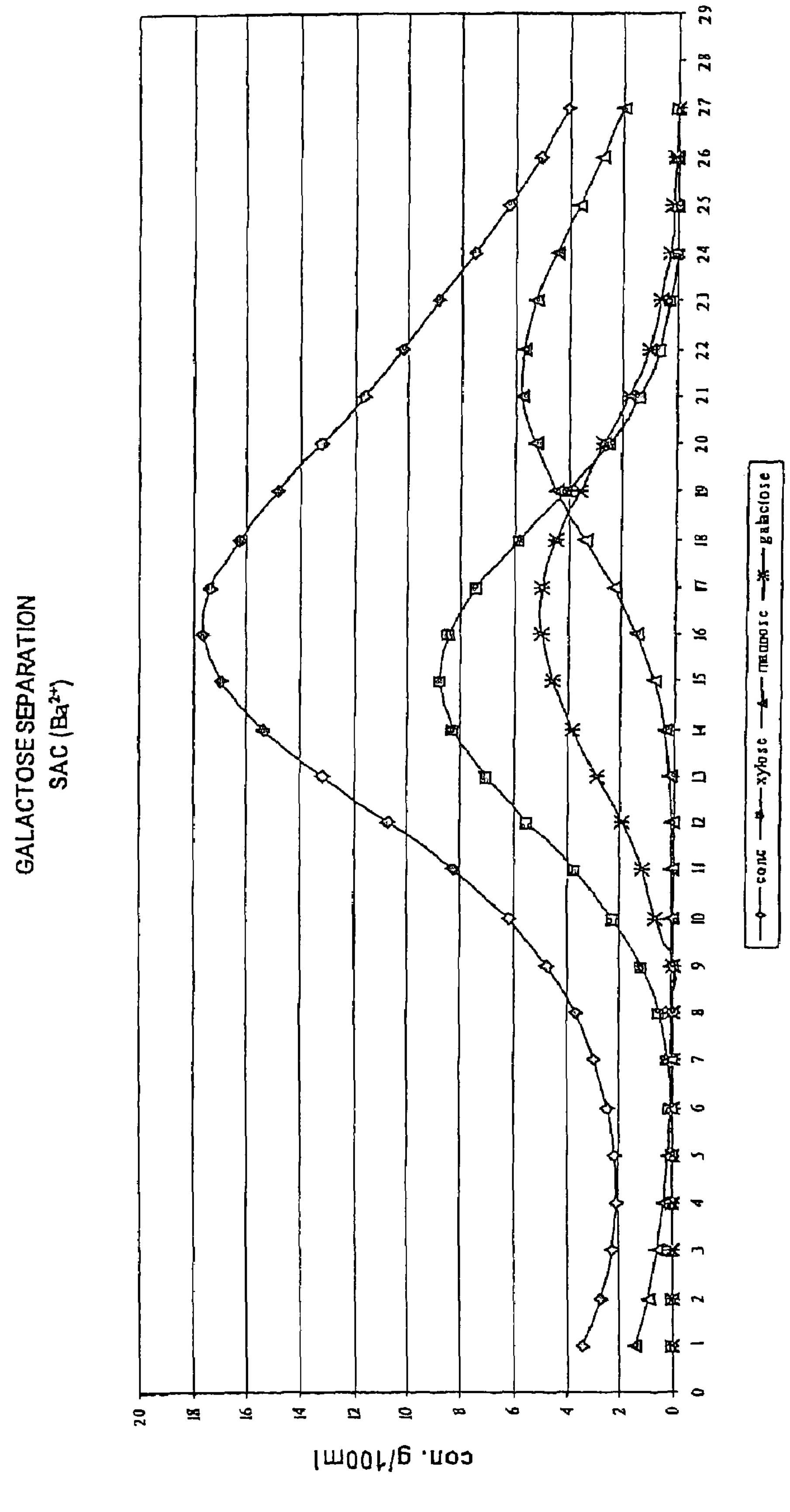
FIG. 5 is a graphical presentation of the separation profile obtained from Example 7 (chromatographic fractionation of a solution containing mainly xylose, galactose and mannose using a strongly acid cation exchange resin in $Ba^{2+}$ form).

The separation profile is presented in FIG. 5. Mannose starts eluting later than other sugars. Thus with a barium-form strongly acidic cation exchange resin galactose and xylose can be separated from mannose.

Example 8

Chromatographic Separation of a Galactose-Containing Solution with a Strongly Acid Cation Exchange Resin in $Pb^{2+}$ Form A solution containing galactose was subjected to chromatographic separation. The separation was performed in a pilot scale chromatographic separation column as a batch process. The column with a diameter of 0.1 m was filled with a strongly acidic cation exchange resin (Finex CA 16 GC, 8.0% DVB) that was in $Pb^{2+}$ form. The height of the resin bed was approximately 1.2 m. The average particle size of the resin was 0.35 mm. The temperature of the column and feed solution and eluent water was 65° C. The flow rate in the column was adjusted to 50 ml/min. The pH of the feed solution was 2.6.

The feed solution had the following composition on DS:

Galactose: 23%
Xylose: 40%
Mannose: 20%
Others: 17%.

The chromatographic separation was carried out as follows:

Step 1: The dry substance of the feed solution was adjusted to 30 g dry substance in 100 g solution according to the refractive index (RI) of the solution.

Step 2: 800 ml of preheated feed solution was pumped to the top of the resin bed.

Step 3: The feed solution was eluted downwards in the column by feeding preheated ion-exchanged water to the top of the column.

Step 4: 50 ml samples of the out-coming solution were collected at 3 min intervals. The composition of the samples was analyzed with HPLC (amino column), and a mixture of water and ACN was used as the eluent.

Figure 6:
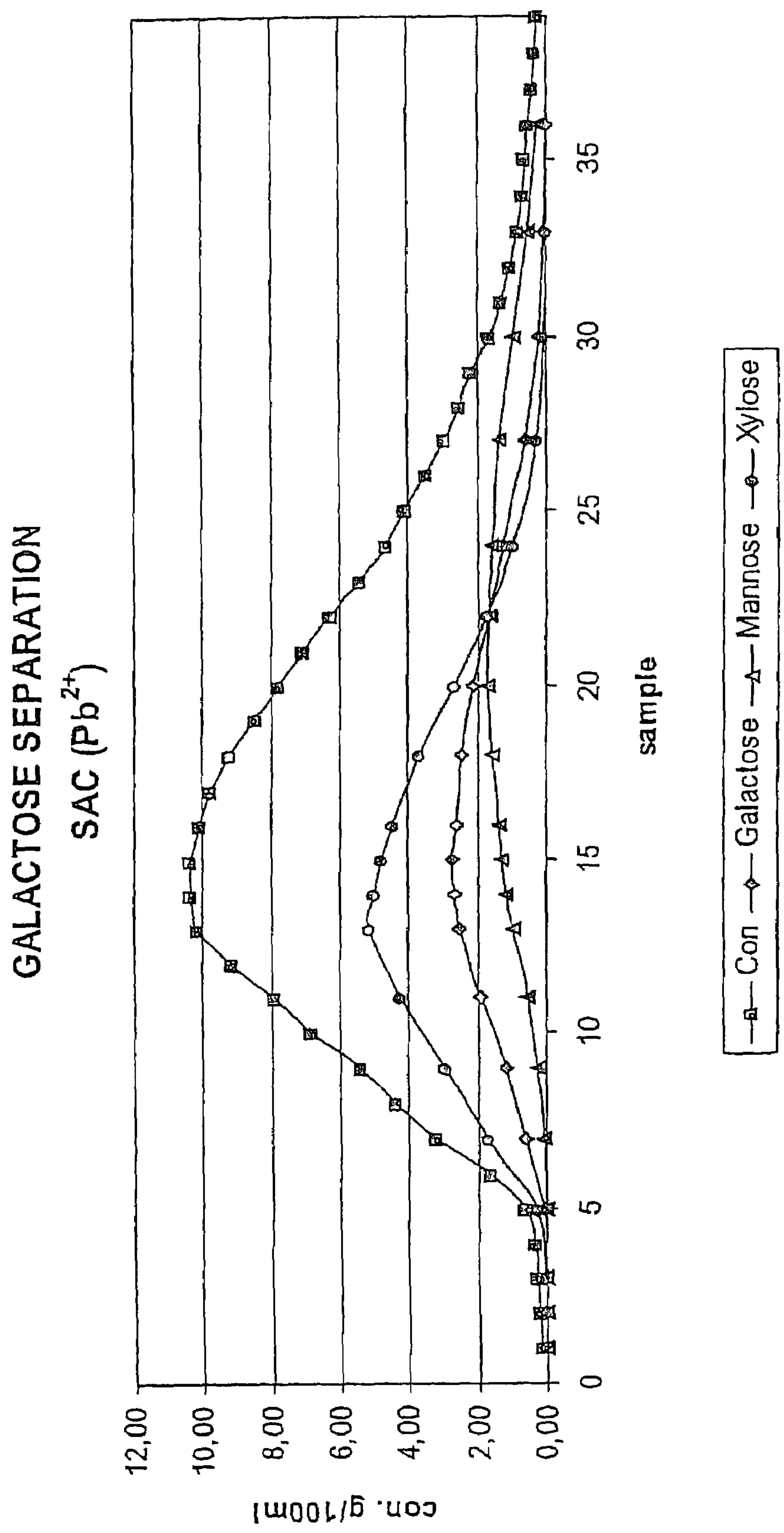
FIG. 6 is a graphical presentation of the separation profile obtained from Example 8 (chromatographic fractionation of a solution containing mainly xylose, galactose and mannose using a strongly acid cation exchange resin in $Pb^{2+}$ form).

The separation profile is presented in FIG. 6. Mannose starts eluting later than other sugars. Thus with a lead-form strongly acid cation exchange resin galactose and xylose can be separated from mannose. The pH of the effluent (e.g. the out-coming solution) was between 3 and 4.

Example 9

Chromatographic Separation of a Galactose-Containing Solution with a Strongly Acid Cation Exchange Resin in $Ba^{2+}$ Form The starting liquor used for the separation of galactose was a galactose-containing side stream separated from a sulphate-form SBA separation made in accordance with Example 1. The solution containing galactose was subjected to chromatographic separation. The separation was performed in a pilot scale chromatographic separation column as a batch process. A column with a diameter of 0.01 m was filled with a strongly acid cation exchange resin (Korela V06, 4% DVB) in $Ba^{2+}$ form. The height of the resin bed was approximately 1.6 m. The average particle size of the resin was 0.25 mm. The temperature of the column and the feed solution and eluent water was 65° C. The flow rate in the column was adjusted to 50 ml/min. The pH of the feed solution was approximately 2.7.

The feed solution (from the separation with a SBA resin in $SO_4^{2-}$ form) had the following composition (based on DS):

Galactose: 58%

Xylose: 1%

Mannose: 18%.

The chromatographic separation was carried out as follows:

Step 1: The dry substance of the feed solution was adjusted to 25 g dry substance in 100 g solution according to the refractive index (RI) of the solution.

Step 2: 600 ml preheated solution was pumped to the top of the resin bed.

Step 3: The feed solution was eluted downwards in the column by feeding preheated ion-exchanged water to the top of the column.

Step 4: Samples of the out-coming solution were collected at 5 min intervals. The composition of the samples was analyzed with HPLC (amino column), and a mixture of water and ACN was used as the eluent.

Figure 7:
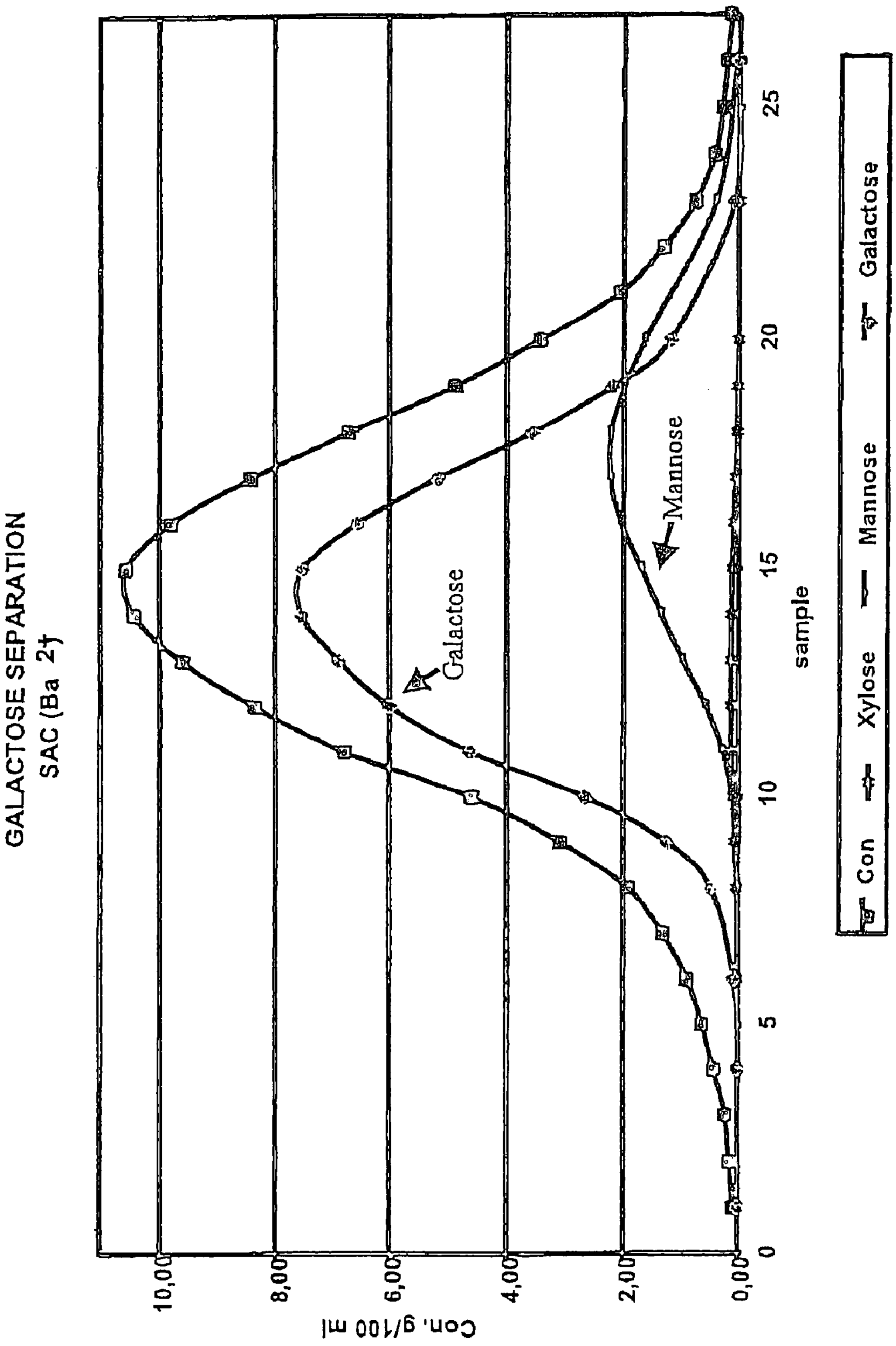
FIG. 7 is a graphical presentation of the separation profile obtained from Example 9 (chromatographic fractionation of a galactose-containing solution based on sulphite spent liquor obtained from the separation with a strongly basic anion exchange resin in $SO_4^{2-}$ form, using a strongly acid cation exchange resin in $Ba^{2+}$ form).

The separation profile is presented in FIG. 7. Mannose starts eluting later than other sugars. Thus with a strongly acid cation exchange resin in $Ba^{2+}$ form, galactose and xylose can be separated from mannose.

Example 10

Chromatographic Separation of a Galactose-Containing Solution with a Strongly Acid Cation Exchange Resin in $Ba^{2+}$ Form The starting liquor used for the separation was a galactose-containing side stream separated from $Ca^{2+}$ based sulphite spent liquor used for the recovery of xylose. Birch had been used as the raw material for the sulphite pulping.

The solution containing galactose was subjected to chromatographic separation. The separation was performed in a plant scale chromatographic separation column as a batch process. The column with a diameter of 2.74 m was filled with a strongly basic anion exchange resin (Finex CS 08 GC, 4.0% DVB). The height of the resin bed was approximately 6.8 m. The average particle size of the resin was 0.3 mm. The resin was regenerated into barium ($Ba^{2+}$)-form. The temperature of the column and feed solution and eluent water was 68° C. The flow rate in the column was adjusted to 690 l/h. The pH of the feed solution was 2.5-2.8.

The feed solution had the following composition on DS:

Galactose: 47%

Xylose: 3%

Mannose: 17%

Glucose: 11%

Others: 22%.

The chromatographic separation was carried out as follows:

Step 1: The dry substance of the feed solution was adjusted to 35 g dry substance in 100 g solution according to the refractive index (RI) of the solution.

Step 2: 1740 l of preheated feed solution was pumped to the top of the resin bed.

Step 3: The feed solution was eluted downwards in the column by feeding preheated ion-exchanged water to the top of the column.

Step 4: Samples of the out-coming solution were collected based on the fraction cuts. The composition of the samples was analyzed with HPLC (amino column), a mixture of water and ACN was used as the eluent.

Fraction data is shown in Table 4. Mannose starts eluting later than other sugars. Thus with a barium-form strongly acidic cation exchange resin galactose and xylose can be separated from mannose. The pH of the effluent (e.g. the out-coming solution) was between 3.3-3.6.

TABLE 4

Fraction data from a chromatographic separation test with a SAC resin in $Ba^{2+}$ form

| | Galactose fraction |
|---|---|
| Volume, l | 3013 |
| Concentration, g/100 ml | 13.2 |
| Galactose, % on RDS | 66.9 |
| Mannose, % on RDS | 11.0 |
| Xylose, % on RDS | 4.3 |
| Glucose, % on RDS | 9.0 |
| Galactose yield, % | 69.6 |
| Mannose yield, % | 30.6 |
| Xylose yield, % | 76.5 |
| Glucose yield, % | 47.7 |

The yield is calculated from all the components eluted from the column.

Example 11

Crystallization of Galactose (1) Crystallization of the First Crystal Crop 32.0 kg of a galactose syrup obtained from one chromatographic separation with a SAC ($Ba^{2+}$)-form resin and two chromatographic separations with an SBA ($SO_4^{2-}$)-form resin and having DS of 35% and a galactose content of 53% on DS, based on the refractometric dry solids content (RDS) of pure galactose, was concentrated by evaporation to RDS of 72% and moved to a 10-liter cooling crystallizer at a temperature of 65° C. Seeding was made to the galactose syrup with 0.05% galactose seed crystals on DS.

The mass was cooled down from a temperature of 60° C. to a temperature of 20° C. The crystallization cake was recovered after 40 hours from seeding by centrifuging, whereby a cake purity of 92.1% on DS was obtained. The centrifuging result corresponds to a 29% dry substance yield. The crystal size was 200 . . . 300 μm.

(2) Purification Crystallization.

1873 g of galactose crystals from the first crop crystallization were dissolved to water. Galactose syrup having a DS of 18% was evaporated to as RDS of 64% and moved to a 2-liter reaction vessel at a temperature of 60° C. Seeding was made to the galactose syrup with 0.02% seeds on DS.

The mass was cooled down from a temperature of 60° C. to a temperature of 20° C. The crystallization cake was recovered after 40 hours from seeding by centrifuging, whereby a cake purity over 99.5% on DS was obtained. The centrifuging result corresponds to a 66% dry substance yield. The crystal size was 300 . . . 500 μm. Crystals were dried in an oven at a temperature of 60° C. for 12 hours. The crystal water content was analyzed to be 0.1%.

(3) Product Crystallization of Galactose 5200 kg of a galactose syrup obtained from chromatographic separation with a SAC ($Ba^{2+}$) form resin, an SBA ($SO_4^{2-}$)-form resin and a SAC ($Ba^{2+}$)-form resin and having DS of 30% and a galactose content of 64% on DS, was evaporated to DS of 72% and moved to 2000 liter cooling crystallizer at 68° C. Seeding (at 68° C., a DS of 73%) was made to the boiling syrup with 0.05% galactose seed crystals on DS.

The mass was cooled down from a temperature of 68° C. to a temperature of 28° C. After 60 hours from seeding, the centrifuging gave a crystal cake purity of 98.3% on DS. The centrifuging result corresponds to a 31% dry substance yield. The crystal size was 100 . . . 200 μm. Crystals were dried in a rotary vacuum dryer at a temperature of 70° C. for 12 hours. The moisture content of the crystals was analyzed to be 0.13%.

Example 12

Chromatographic Fractionation of a Gum Arabic Hydrolyzate with a Weakly Acid Cation Exchange Resin (WAC Resin) in $H^+$ Form and Crystallization of Galactose from the Galactose Fraction The feed solution for the separation was a gum arabic hydrolyzate prepared from Gum Arabic Seyal. The hydrolyzate, which mainly contained arabinose, galactose and rhamnose, had been neutralized with $Ca(OH)_2$ and NaOH and filtered with diatomaceous earth.

The feed solution had the following composition (% on RDS):

| | |
|---|---|
| Arabinose | 37.8 |
| Galactose | 16.9 |
| Rhamnose | 2.4 |
| Others | 42.9 |

The solution having the composition presented above was subjected to chromatographic separation. The separation was performed in a pilot scale chromatographic separation column as a batch process. The column with a diameter of 0.2 m was filled with a weakly acid cation exchange resin (Finex CA 16 GC, 8% DVB). The height of the resin bed was approximately 15.8 m. The average particle size of the resin was 0.308 mm. The resin was regenerated into hydrogen ($H^+$) form with 5% HCl. The temperature of the column, the feed solution and the eluent water was 60° C. The flow rate in the column was adjusted to 60 l/h. The pH of the feed solution was 4.

The chromatographic separation was carried out as follows:

Step 1: The dry substance of the feed solution was adjusted to 45 g dry substance in 100 g solution according to the refractive index (RI) of the solution.

Step 2: 28 l of preheated feed solution was pumped to the top of the resin bed.

Step 3: The feed solution was eluted downwards in the column by feeding preheated ion-exchanged water to the top of the column.

Step 4. 5 ml samples of the out-coming solution were collected at 5 min intervals. The composition of the samples was analyzed with HPLC equipment provided with a refractive index detector and an $Na^+$ SAC column (water was used as the eluent).

Figure 8:
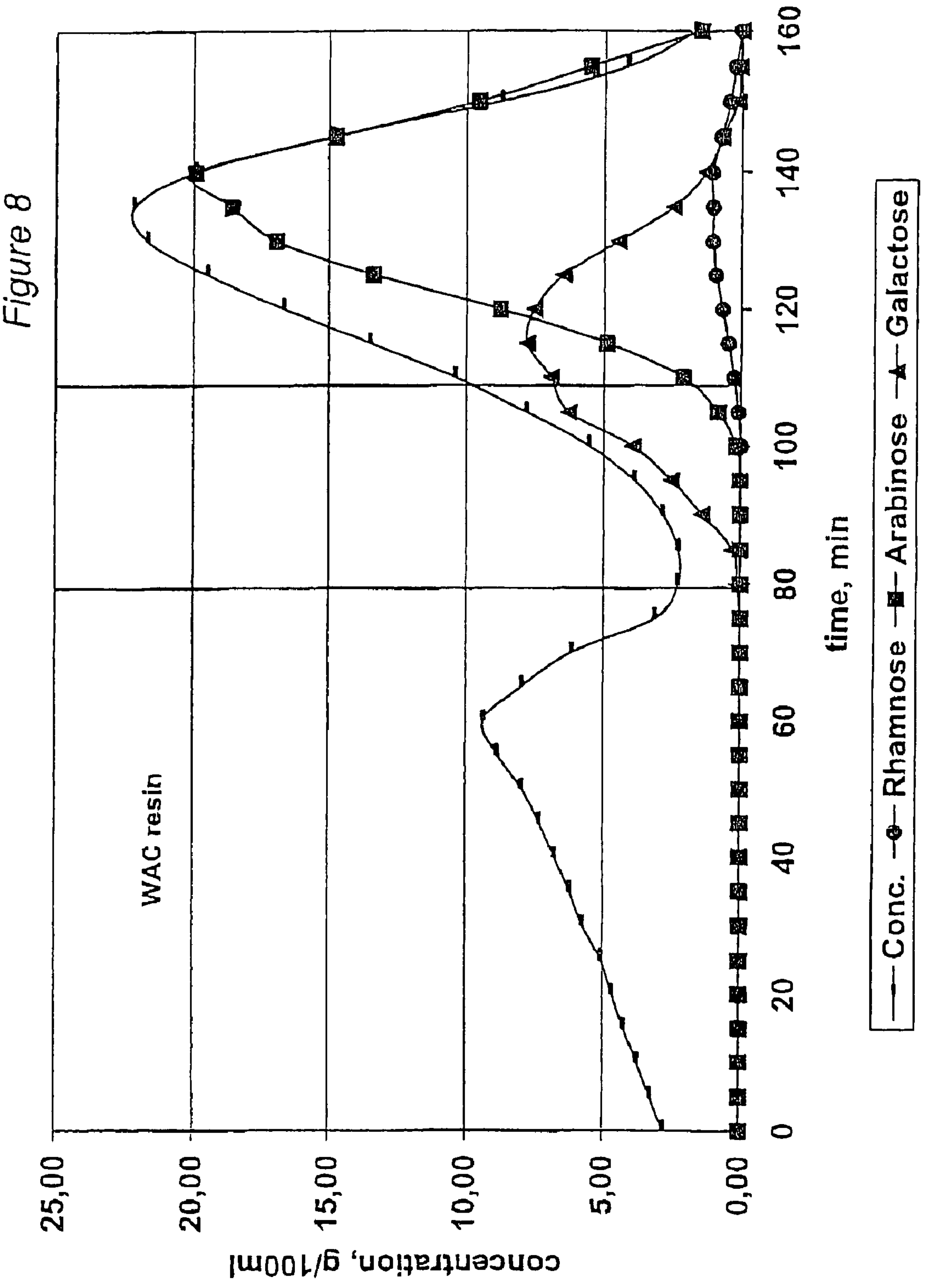
FIG. 8 is a graphical presentation of the separation profile obtained from Example 12 (chromatographic fractionation of a gum Arabic hydrolyzate with a weakly acid cation exchange resin in $H^+$ form).

The separation profile is presented in FIG. 8 and fraction data in Table 5. Elution begins with salts and poly-, oligo- and disaccharides, followed by the elution of monosaccharides in the order: galactose, arabinose and rhamnose. Since galactose elutes earlier than the others, galactose and arabinose can thus be separated from gum arabic matrix with a weakly acid cation exchange resin in acidic conditions. For example, galactose and arabinose fractions presented in the following table may be collected in addition to residual fractions. The yield of a component in a fraction is presented in relation to the total amount of that component in all out-coming fractions, calculated from the analysis of the elution profile samples.

TABLE 5

Fraction data from a chromatographic separation test with a WAC resin in $H^+$ form

| | Galactose fraction | Arabinose fraction |
|---|---|---|
| Volume, I | 22 | 65 |
| Concentration, g/100 ml | 4.7 | 11.1 |
| Composition, % on RDS | | |
| Arabinose | 5 | 70 |
| Galactose | 66 | 24 |
| Rhamnose | 0 | 4 |
| Others | 29 | 2 |
| Yield, % | | |
| Arabinose | 1 | 99 |
| Galactose | 28 | 71 |

The pH of the effluent (i.e. the out-coming solution) was 2.7 to 4.6.

Galactose is crystallized from the galactose fraction having a galactose content of 66% on DS as follows:

The galactose fraction obtained above is evaporated to RDS of 72% and moved to a 10-liter cooling crystallizer at a temperature of 70° C. Seeding (at 70° C., an RDS of 72%) is made to a boiling syrup with 0.05% galactose seed crystals on DS.

The mass is cooled down from the temperature of 70° C. to a temperature of 20° C. The galactose crystals are separated after 50 hours from seeding by centrifugation. The yield of galactose is about 65%.

The crystals of the first crystal crop thus obtained are dissolved in water to obtain a galactose syrup having a DS of 18%. The syrup is evaporated to an RDS of 63% and moved to a 2-liter reaction vessel at a temperature of 70° C. Seeding (at 70° C., an RDS of 63%) is made to a boiling syrup with 0.02% seeds on DS.

The mass is cooled down from the temperature of 70° C. to a temperature of 20° C. The galactose crystals are separated after 40 hours from seeding by centrifugation. The galactose crystals thus obtained are dried in an oven at a temperature of 60° C. for 12 hours. The galactose yield is about 65%.

Example 13

Comparative Analysis of the Monosaccharide (Sugar) Impurities of the Crystalline D-Galactose of the Invention and Commercial Galactose Samples Samples of crystalline D-galactose of the invention (based on calcium sulphite spent liquor) as well as samples of comparative commercial mannose crystals were subjected to monosaccharide assay. The monosaccharides (D-galactose as well the impurities D-xylose, L-arabinose, L-rhamnose and D-mannose) were determined by HPLC (Dionex), anion exchange column (PA1) and electrochemical detector (PED). D-glucose was determined by HPLC, Pb-column and refractometric detector. The analysis results are presented in Table 6.

In Table 6, samples 1, 2, 3 and 4 represent crystalline D-galactose of the invention. Sample 1 was obtained by chromatographic fractionation in accordance with Example 2 (SBA resin in $SO_4^{2-}$ form) followed by crystallization in accordance with Example 11(3). Sample 2 was obtained by chromatographic fractionation in accordance with Example 2 (SBA resin in $SO_4^{2-}$ form) followed by crystallization in accordance with Example 11(2). Samples 3 and 4 were obtained by chromatographic fractionation in accordance with Examples 3 and 10 (separation with an SBA resin in $SO_4^{2-}$ form and separation with a SAC resin in $Ba^{2+}$ form) followed by similar crystallization in accordance with example 11(2).

Comparison galactose samples were samples of commercial D-galactose manufactured by Sigma and BDH.

Furthermore, an additional sample of the invention (sample 5) was subjected to monosaccharide assay with HPLC, amino column and refractometric detector. Sample 5 was obtained by chromatographic fractionation in accordance with Examples 3 and 10 (separation with an SBA resin in $SO_4^{2-}$ form and separation with a SAC resin in $Ba^{2+}$ form) followed by similar crystallization in accordance with Example 11(1). The results are presented in Table 7.

It will be obvious to a person skilled in the art that, as the technology advances, the inventive concept can be implemented in various ways. The invention and its embodiments are not limited to the examples described above but may vary within the scope of the claims.

The invention claimed is:

1. A process of recovering galactose from a plant-based hemicellulose hydrolyzate solution containing a galactose content of at least 5% by weight, said process comprising (a) subjecting said solution to chromatographic fractionations, said chromatographic fractionations comprising one or more fractionations using a strongly basic anion exchange resin, wherein the anion is selected from $SO_4^{2-}$, $SO_3^{2-}$, $HSO_3^-$, $CH_3COO^-$, and one or more fractionations using a cation exchange resin, wherein the cation exchange resin is selected from strong or weak cation exchange resin;

(b) recovering at least one fraction enriched in galactose, having a galactose content of 38 to 95% on RDS;

(c) subjecting said at least one fraction enriched in galactose to crystallization; and (d) recovering a plant-based crystalline galactose product having a purity of more than 90% on DS.

2. A process as claimed in claim 1, wherein said one or more chromatographic fractionations comprise one or more chromatographic fractionation steps using a column filling material selected from strongly basic anion exchange resins in $HSO_3^-$ form.

3. A process as claimed in claim 2, wherein said one or more chromatographic fractionations comprise two chromatographic fractionation steps with a resin in $HSO_3^-$ form.

4. A process as claimed in claim 1, wherein the ion form of said cation exchange resin is selected from $Ba^{2+}$, $Pb^{2+}$, $Ca^{2+}$ and $Sr^{2+}$.

5. A process as claimed in claim 1, wherein said one or more chromatographic fractionations comprise one or more chromatographic fractionation steps using a column filling material selected from strongly basic anion exchange resins and one or more chromatographic fractionation steps using a column filling material selected from strongly acid cation exchange resins, in any desired sequence.

TABLE 6

| Content of monosaccharide impurities of galactose crystal samples (% on DS) | | | | | | | |
|---|---|---|---|---|---|---|---|
| Galactose samples | D-Galactose | L-Fucose | L-Rhamnose | L-Arabinose | D-Mannose | D-Glucose | D-Xylose |
| Sample 1 | 98.3 | <0.01 | 0.03 | 0.40 | 0.22 | 0.35 | — |
| Sample 2 | 99.5 | <0.01 | <0.01 | 0.29 | 0.05 | 0.25 | — |
| Sample 3 | 98.5 | — | 0.08 | 0.18 | 0.23 | 0.23 | 0.17 |
| Sample 4 | 97.5 | — | 0.10 | 0.18 | 0.32 | 0.22 | 0.19 |
| Sigma G-0625, lot 042K0130 | 95.3 | <0.01 | — | — | <0.01 | 0.62 | — |
| BDH, lot 1353890 | 82.3 | 0.04 | — | <0.01 | — | 1.46 | — |
| Sigma G-6404, lot 73H02713 | 94.6 | <0.01 | <0.01 | — | — | 0.60 | — |

TABLE 7

| Content of monosaccharide impurities of galactose crystal samples (% on DS) | | | | | | | |
|---|---|---|---|---|---|---|---|
| Galactose sample | D-Galactose | L-Rhamnose | L-Fucose | D-Xylose | L-Arabinose | D-Fructose | D-Mannose |
| Sample 5 | 94.3 | 0.37 | 0.06 | 0.33 | 0.28 | 0.03 | 0.95 |

6. A process as claimed in claim 1, wherein the crystallization is carried out using a solvent selected from water and a mixture of water and alcohol as the crystallization solvent.

7. A process as claimed in claim 6, wherein the crystallization solvent is a mixture of ethanol and water.

8. A process as claimed in claim 6, wherein the crystallization solvent is water.

9. A process as claimed in claim 1, wherein the crystallization provides crystalline galactose having a purity of more than 95% on DS.

10. A process as claimed in claim 1, wherein the crystallization provides crystalline galactose having a purity of more than 98% on DS.

11. A process as claimed in claim 1, wherein the crystallization provides crystalline galactose having a purity of more than 99.5% on DS.

12. A process as claimed in claim 1, wherein the crystallization provides crystalline galactose having a maximum content of D-glucose of 0.50% on DS.

13. A process as claimed in claim 1, wherein the crystallization provides crystalline galactose having a maximum content of D-glucose of 0.30%.

14. A process as claimed in claim 1, wherein the crystallization provides crystalline galactose having an impurity profile comprising at least one sugar selected from xylose, arabinose, rhamnose and mannose.

15. A process as claimed in claim 14, wherein the crystallization provides crystalline galactose, where the impurity profile comprises at least one of said sugars in an amount of 0.03% on DS or more.

16. A process as claimed in claim 15, wherein the crystallization provides crystalline galactose, where the impurity profile comprises arabinose in an amount of 0.03% on DS or more.

17. A process as claimed in claim 15, wherein the crystallization provides crystalline galactose, where the impurity profile comprises mannose in an amount of 0.03% on DS or more.

18. A process as claimed in claim 14, wherein the crystallization provides crystalline galactose, where the impurity profile comprises at least one of said sugars in an amount of 0.10% or more.

19. A process as claimed in claim 1, wherein the process further comprises one or more purification steps selected from membrane filtration, ion exchange, evaporation and filtration carried out before, after or between said chromatographic fractionation step/steps.

20. A process as claimed in claim 1, wherein the process further comprises crystallization between said chromatographic fractionation steps.

21. A process as claimed in claim 20, wherein said crystallization comprises precipitation crystallization of xylose.

22. A process as claimed in claim 1, wherein said plant-based hemicellulose hydrolysate is hydrolysate derived from wood material.

23. A process as claimed in claim 1, wherein said plant-based hemicellulose hydrolysate is a hydrolysate derived from softwood or hardwood.

24. A process as claimed in claim 1, wherein said solution derived from the plant-based hemicellulose hydrolyzate is a spent liquor obtained from a pulping process.

25. A process as claimed in claim 24, wherein said spent liquor obtained from a pulping process is a spent sulphite pulping liquor.

26. A process as claimed in claim 25, wherein said spent sulphite pulping liquor is a spent sulphite pulping liquor recovered after the separation of the main part of xylose.

27. A process as claimed in claim 1, wherein said solution derived from the plant-based hemicellulose hydrolyzate contains galactose and one or more further sugars selected from arabinose and mannose.

28. A process as claimed in claim 1, wherein said galactose is D-galactose.

29. A process as claimed in claim 14, wherein said xylose is D-xylose, said arabinose is L-arabinose, said mannose is D-mannose and said rhamnose is L-rhamnose.

* * * * *